United States Patent
Turner et al.

(10) Patent No.: US 12,239,774 B2
(45) Date of Patent: Mar. 4, 2025

(54) HEATER-COOLER SYSTEM

(71) Applicant: Spectrum Medical Ltd., Gloucester (GB)

(72) Inventors: Stephen Turner, Gloucester (GB); Benjamin David Garbutt, Gloucester (GB)

(73) Assignee: SPECTRUM MEDICAL LTD., Gloucester (GB)

( * ) Notice: Subject to any disclaimer, the term of this patent is extended or adjusted under 35 U.S.C. 154(b) by 1417 days.

(21) Appl. No.: 16/629,664

(22) PCT Filed: Jul. 17, 2018

(86) PCT No.: PCT/GB2018/052027
§ 371 (c)(1),
(2) Date: Jan. 9, 2020

(87) PCT Pub. No.: WO2019/016542
PCT Pub. Date: Jan. 24, 2019

(65) Prior Publication Data
US 2021/0154389 A1    May 27, 2021

(30) Foreign Application Priority Data
Jul. 19, 2017   (GB) .................................. 1711613

(51) Int. Cl.
*A61M 1/36*   (2006.01)
*B01D 19/00*  (2006.01)

(52) U.S. Cl.
CPC .......... *A61M 1/369* (2013.01); *A61M 1/3633* (2013.01); *B01D 19/00* (2013.01);
(Continued)

(58) Field of Classification Search
CPC .... A61M 1/369; A61M 1/36; A61M 1/36223; A61M 2205/3606; A61M 2205/366;
(Continued)

(56) References Cited

U.S. PATENT DOCUMENTS 4,479,798 A    10/1984  Parks
5,674,190 A *  10/1997  Kelly .................... A61M 1/369
                                              607/106
(Continued)

FOREIGN PATENT DOCUMENTS

EP    1245247 A1 * 10/2002 ............. A61L 29/14
EP    1487387 A1   12/2004
(Continued)

OTHER PUBLICATIONS

European Patent Office. Extended European Search Report for application 21167551.7. Mailed on Jun. 8, 2021. 13 pages.
(Continued)

*Primary Examiner* — Andrew J Mensh
*Assistant Examiner* — Ted Yang
(74) *Attorney, Agent, or Firm* — QUARLES & BRADY LLP

(57) ABSTRACT

A heater-cooler apparatus of an extracorporeal perfusion system comprises at least one fluid circuit (102, 104) providing a supply of a heat transfer fluid to the perfusion system, a cold storage unit (266), and a refrigeration unit (250) for charging the cold storage unit (266). The cold storage unit (266) comprises a chamber (312) containing a liquid that freezes at a temperature above that to which the heat transfer fluid is cooled by the refrigeration unit (250), and a passage through which the heat transfer fluid is conveyed, the passage extending through the chamber (312). This allows a more effective cold storage unit to be provided.

24 Claims, 16 Drawing Sheets

(52) U.S. Cl.
CPC . *A61M 2205/11* (2013.01); *A61M 2205/3331* (2013.01); *A61M 2205/3606* (2013.01); *A61M 2205/366* (2013.01)

(58) Field of Classification Search
CPC .......... F28F 13/00; F28F 3/14; F28F 2210/04; A61F 2007/0056
See application file for complete search history.

(56) References Cited

U.S. PATENT DOCUMENTS

| | | | |
|---|---|---|---|
| 5,817,045 | A | 10/1998 | Sever |
| 5,948,012 | A * | 9/1999 | Mahaffey ................. A61F 7/10 607/104 |
| 6,205,807 | B1 * | 3/2001 | Broadbent ................ F28F 3/14 62/352 |
| 6,423,268 | B1 | 7/2002 | King |
| 2006/0030917 | A1 | 2/2006 | Eccleston |
| 2007/0197951 | A1 * | 8/2007 | Mannlein ................ A61M 5/44 604/6.13 |
| 2009/0235686 | A1 | 9/2009 | Kikuchi |
| 2013/0090708 | A1 * | 4/2013 | Dabrowiak .............. A61F 7/12 607/105 |
| 2013/0272924 | A1 * | 10/2013 | Platt ..................... A61M 1/369 607/104 |
| 2013/0319464 | A1 * | 12/2013 | Barrett ................... F28F 19/01 210/167.01 |
| 2014/0102672 | A1 * | 4/2014 | Campbell ......... H05K 7/20836 165/104.19 |
| 2016/0184132 | A1 * | 6/2016 | Platt .................... A61F 7/0085 607/104 |
| 2016/0242957 | A1 | 8/2016 | Schaefer |

FOREIGN PATENT DOCUMENTS

| | | | | |
|---|---|---|---|---|
| FR | 2721218 | A3 | 12/1995 | |
| GB | 2551795 | A | 1/2018 | |
| GB | 2551877 | A | 1/2018 | |
| GB | 2552064 | A | 1/2018 | |
| WO | 1997006840 | A1 | 2/1997 | |
| WO | WO-2016026525 | A1 * | 2/2016 | ............ A01N 59/00 |
| WO | 2016195651 | A1 | 12/2016 | |
| WO | 2018002622 | A1 | 1/2018 | |
| WO | 2019068342 | A1 | 4/2019 | |
| WO | 2010111778 | A1 | 10/2020 | |

OTHER PUBLICATIONS

Sommerstein, R., et al. "Transmission of *Mycobacterium chimaera* from heater-cooler units during cardiac surgery despite an ultraclean air ventilation system." Emerging infectious diseases 22.6 (2016): 1008.

Food and Drug Administration "Nontuberculous *Mycobacterium* (NTM) Infections Associated with Heater-Cooler Devices (HCD) during Cardiothoracic Surgery", FDA Executive Summary, Jun. 2-3, 2016, Circulatory Devices Panel of the Medical Devices Advisory Committee.

International Bureau of WIPO, International Preliminary Report on Patentability for application GB2018/052027, mailed on Jan. 30, 2020. 23 pages.

Intellectual Property Office, Search Report for application GB1711613.8, mailed on Jan. 31, 2018. 5 pages.

Intellectual Property Office, Search Report for application GB2019946.9, mailed on Feb. 10, 2021. 4 pages.

* cited by examiner

HEATER-COOLER SYSTEM

CROSS REFERENCE TO RELATED APPLICATIONS

This application represents the U.S. national stage entry of PCT/GB2018/052027 filed Jul. 17, 2018, which claims benefit of United Kingdom application 1711613.8 filed Jul. 19, 2017. The contents of these applications are hereby incorporated by reference as set forth in their entirety herein.

FIELD OF THE INVENTION

The present invention relates to a heater-cooler apparatus and associated method used in medical/surgical procedures for cooling and heating blood or other fluids in an extracorporeal perfusion system.

BACKGROUND

During surgical procedures, heater-cooler systems are used to set the temperature of extracorporeal circulating fluids before they are returned to a patient. During surgery, for instance, a patient's body may be cooled by induced hypothermia to as low as perhaps 15 degrees Celsius, below the normal body temperature of 37 degrees Celsius, to reduce metabolic activity. Conversely, other parts of the body, such as an isolated limb or the peritoneal cavity, may be selectively warmed to a temperature exceeding 37 degrees, or less than 37 degrees.

Conventional heater-cooler systems comprise one or more water baths to supply temperature-controlled water as a heat transfer medium through a medical device, such as through an extracorporeal oxygenator, through a cardioplegia unit ("cardioplegic" meaning heartbeat-suppressing), or through a stand-alone heat exchanger, in order to control the temperature of fluid administered to a patient. For instance, oxygenators comprise a heat exchange mechanism with connectors for receiving temperature-controlled water as a heat transfer medium from the heater-cooler system, to set the temperature of blood oxygenated in an oxygenator so that the temperature is suitable for subsequent administration to a patient. Similarly, cardioplegia, isolated limb perfusion, left-heart bypass, and other procedures use heat exchangers to control blood temperature.

Recent world health advisories and independent group studies confirm that currently marketed heater-cooler solutions are linked to elevated contamination risks and health hazards and point to the need for new heater-cooler technologies that eliminate contamination while delivering on vital heating and cooling performance (see: reference 1—"Transmission of *Mycobacterium chimaera* from Heater-Cooler Units during Cardiac Surgery despite an Ultraclean Air Ventilation System", Emerging Infectious Diseases, Vol. 22, No. 6, June 2016; and reference 2—"Non-tuberculous Mycobacterium (NTM) Infections Associated with Heater-Cooler Devices (HCD) during Cardiothoracic Surgery", FDA Executive Summary, Jun. 2-3, 2016, Circulatory Devices Panel of the Medical Devices Advisory Committee).

Although water-based heater-cooler systems may comprise sealed flow systems that prevent any possibility of contamination being transferred through the equipment while it is in use during surgery, the set-up and removal of the equipment before or after surgery can result in microbes being released in water vapour into the operating theatre environment. Disposable components may be used in some parts of the systems, but it is not practical (and would be hugely expensive) for the entire heater-cooler apparatus to be provided as a sterile and disposable unit.

Conventional heater-cooler systems include cooling devices, such as refrigeration units for providing a cooled flow of heat transfer fluid when it is required to reduce temperatures (e.g. the patient's blood temperature). Refrigeration units employ compressors, in a refrigerant flow circuit. Compressors themselves require external cooling, which is usually provided in the form of an air flow from a cooling fan. However, many surgical procedures employ a laminar air curtain over the patient to provide a barrier against airborne microbial infection. Having a compressor cooling fan in close proximity can disrupt such an air curtain.

The present invention is concerned with improving the temperature management and control of a heater-cooler system for use in an extracorporeal perfusion system while reducing or eliminating contamination risks.

GB2551877A discloses a heater cooler apparatus for a perfusion system where the heater cooler apparatus comprises a heater cooler device and an antimicrobial fluid.

WO2010/111778A1 discloses a system, apparatus and methods for extra-corporeal blood treatment.

WO2016/195651A1 discloses systems, apparatus and methods relating to use of a local perfusion extracorporeal circuit for perfusing a local target region of a body.

WO97/06840A1 discloses a perfusion hyper/hypothermia treatment system.

US2009/235686A1 discloses a fluid temperature regulator.

U.S. Pat. No. 5,817,045A discloses an apparatus and method for using an apparatus for extracorporeal therapeutic treatment of changing volume of up to at least about half of the circulating blood of a living patient at one time.

U.S. Pat. No. 4,479,798A discloses a process of hyperthermic treatment of a patient.

EP1487387A1 discloses a temperature control system providing optimal management of patient temperature during a surgical procedure.

US2007/197951A1 discloses a rotary valve unit for blending fluid sources to regulate a temperature of fluid flowing to a heat exchange device in an extracorporeal blood perfusion circuit.

U.S. Pat. No. 6,423,268B discloses a blood heating system for use in open heat surgery.

SUMMARY OF THE INVENTION

To overcome the increased risks of health hazards, leading to death in some cases (see References 1 and 2 mentioned above), from contamination issues associated with known heater-cooler devices, the present invention provides a heater-cooler system (HCS) with a closed loop heat transfer fluid circuit. Embodiments of the invention do not support bacterial growth and endotoxins, have acceptable low levels of chemical contaminants, and safely and effectively provide heating & cooling demands for patient cardioplegia and oxygenator circuits.

According to a first aspect of the invention there is provided a heater-cooler apparatus of an extracorporeal perfusion system. The heater-cooler apparatus comprises: at least one fluid circuit providing a supply of a heat transfer fluid to the perfusion system; a cold storage unit; and a refrigeration unit for charging the cold storage unit.

The cold storage unit preferably comprises a non-water-based phase change material that freezes when cooled. The latent heat removed from the material provides a substantial store of cooling.

It is an advantage that, by including a cold storage unit, cooling can be provided by drawing from the cold store without the need to operate a compressor. This ensures that there can be no disturbance of a laminar air curtain over the patient's body caused by a compressor fan.

In embodiments the heater-cooler apparatus comprises flow circuitry for directing the heat transfer fluid through the refrigeration unit to cool the heat transfer fluid and through the cold storage unit to charge the cold storage unit. Charging of the cold storage unit may be performed prior to use of the apparatus for extracorporeal perfusion. Preferably the flow circuitry is further configured to direct heat transfer fluid through the cold storage unit to cool the heat transfer fluid for use in the extracorporeal perfusion system without the heat transfer fluid being cooled by the refrigeration unit.

In some embodiments the heater-cooler apparatus may comprise an integral unit that includes the refrigeration unit. Alternatively, the refrigeration unit may be provided as a separate unit for supplying a flow of cooled heat transfer fluid to charge the cold storage unit. It can be advantageous to provide a separate refrigeration unit that can be kept remote from the operating theatre for the purpose of charging the cold storage unit.

In embodiments the heater-cooler apparatus may further comprise one or more heaters for heating the heat transfer fluid. These heaters are provided for situations where it is required to provide heated heat transfer fluid to the extracorporeal perfusion system.

In embodiments the heater-cooler apparatus comprises a plurality of fluid circuits for supplying cooled (or heated) heat transfer fluid to a plurality of heat exchangers of the perfusion system. For example one circuit may supply an oxygenator and another circuit may supply a cardioplegia unit.

In embodiments the heat transfer fluid is a biocidal fluid. The biocidal fluid may comprise glycol. The use of a biocidal fluid helps to ensure that microbial infections cannot be transmitted through the heater-cooler apparatus into the perfusion system. In such embodiments the fluid circuits may provide heat transfer fluid directly from the heater-cooler apparatus to heat exchangers of the extracorporeal perfusion system. For example, the heater-cooler system may supply the heat transfer fluid directly to an oxygenator and to a cardioplegia unit, with these units being specifically designed and approved for use with the biocidal fluid. Alternatively, the fluid circuits may provide heat transfer fluid to a disposable heat-exchanger module supplied with the heat transfer fluid from the heater-cooler apparatus. This allows use of the heater-cooler apparatus with apparatus that is approved for use with other fluids (such as sterilised water).

In embodiments the cold storage unit may comprise a chamber containing a liquid that freezes at a temperature above that to which the heat transfer fluid is cooled by the refrigeration unit, and a passage through which the heat transfer fluid is conveyed, the passage extending through the chamber. The passage may comprise or may be constituted by an array of tubes. The cold storage unit may further comprise fins extending around and between tubes of the array of tubes.

Embodiments may further comprise a sensor for providing an indication of a state of charge of the cold storage unit. The sensor may be a level sensor for measuring a level of the cold storage material in the chamber, or a pressure sensor for measuring a pressure in the chamber. Such embodiments may further comprise a controller configured to determine a duration of operation of the apparatus based on the determined state of charge and on one or more physiological parameters of a patient. The physiological parameters may comprise a weight of the patient or a body mass index of the patient.

Embodiments of the heater-cooler apparatus may further comprise a circuit for circulation of heat transfer fluid through a de-aerator and filter and a reservoir of heat transfer fluid for replenishing heat transfer fluid in the heater-cooler apparatus.

According to a second aspect of the invention there is provided a method of operating a heater-cooler apparatus according to the first aspect, as set forth in claim 20. The method comprises: a charging stage, including operating the refrigeration unit to charge the cold storage unit and ceasing operation of the refrigeration unit; and an operating stage including directing heat transfer fluid through the cold storage unit to cool the heat transfer fluid for use in the extracorporeal perfusion system.

The method may further comprise monitoring a state of charge of the cold storage unit. The state of charge of the cold storage unit may be monitored by measuring a level of the cold storage material in the cold storage unit, or by measuring a pressure in the chamber of cold storage unit. In embodiments the method may further comprise determining a duration of operation of the apparatus based on the determined state of charge of the cold storage unit and on one or more physiological parameters of a patient. The physiological parameters may comprise a weight of the patient or a body mass index of the patient.

In some embodiments the method may further comprise filling a heat transfer fluid reservoir of the heater-cooler system during the charging stage.

According to a third aspect of the present invention there is provided a heater-cooler apparatus for an extracorporeal perfusion system that comprises a first device requiring temperature-control and a second device requiring temperature control, as set forth in claim 26. The apparatus comprises a thermal generator unit simultaneously providing separate supplies of heat transfer fluid, one at a higher temperature and one at a lower temperature, to respective hot and cold flow circuits. First and second controlled off-takes are provided from each of the hot and cold flow circuits. The first controlled off-takes are configured to provide a first flow of heat transfer fluid to a first intermediate heat exchanger. The second controlled off-takes are configured to provide a second flow of the heat transfer fluid to a second intermediate heat exchanger. The first intermediate heat exchanger exchanges heat between the first flow of heat transfer fluid and a first intermediate fluid, which circulates in a closed loop that passes through the first device. The second intermediate heat exchanger exchanges heat between the second flow of heat transfer fluid and a second intermediate fluid, which circulates in a closed loop that passes through the second device.

It is an advantage that the heater-cooler operates closed circuits of heat transfer fluid that do not support bacteria growth and have acceptable very low (i.e. negligible) levels of endotoxins and chemical contaminants. It is a further advantage that the heater-cooler apparatus simultaneously provides a hot (higher temperature) and a cold (lower temperature) supply of fluid enabling a fast response to changes in demand for either heating or cooling at the perfusion devices.

The first device may be an oxygenator and the second device may be a cardioplegia unit.

One or more of the controlled off-takes may comprise a control valve.

The thermal generator unit may be configured to provide the separate supplies of heat transfer fluid, one at a higher temperature and another at a lower temperature, to a mixer unit, wherein the mixer unit is adapted to mix the supplied heat transfer fluid to provide the first and second flows of heat transfer fluid to the first and second intermediate heat exchangers.

The thermal generator unit may comprise a heater module for heating the heat transfer fluid. The thermal generator unit may comprise a refrigeration module for cooling the heat transfer fluid. The refrigeration module may be further adapted to heat the heat transfer fluid when so required. The thermal generator unit may comprise a heat pump for transferring heat from the supply of heat transfer fluid at the lower temperature to the supply of heat transfer fluid at the higher temperature.

The heater-cooler apparatus may further comprise a radiator for exchanging heat between heat transfer fluid caused to flow through the radiator and ambient air.

The hot flow circuit may comprise a first pump and a first 3-way control valve, and the cold flow circuit that comprises a second pump and a second 3-way control valve, wherein operation of the first 3-way control valve diverts flow of heat transfer fluid from the hot flow circuit through the radiator so as to remove excess heat from the heat transfer fluid, and wherein operation of the second 3-way control valve diverts flow of heat transfer fluid from the cold flow circuit through the radiator so as to draw in heat to the heat transfer fluid from the ambient air.

The heater-cooler apparatus may further comprise a controller adapted to control the thermal generator unit to provide the separate supplies of heat transfer fluid at the higher and lower temperatures. The controller may be adapted to control each of said controlled off-takes to provide the first and second flows of heat transfer fluid. The controller may be adapted to independently control the flows and temperatures of the first and second intermediate fluids provided to the oxygenator and cardioplegia unit.

The heat transfer fluid may be a biocidal fluid. The biocidal fluid may comprise glycol.

According to a fourth aspect of the present invention there is provided a method of providing thermal control of fluids in an extracorporeal perfusion system that comprises a first device requiring temperature-control and a second device requiring temperature control, as set forth in claim 40. The method comprises: simultaneously providing separate supplies of heat transfer fluid, one at a higher temperature and one at a lower temperature, to respective hot and cold flow circuits; controlling off-takes from each of said hot and cold flow circuits to provide a first flow of heated or cooled heat transfer fluid to a first intermediate heat exchanger and a second flow of heated or cooled heat transfer fluid to a second intermediate heat exchanger; exchanging heat between the first flow of heat transfer fluid and a first intermediate fluid that circulates in a closed loop through said first device, and exchanging heat between the second flow of heat transfer fluid and a second intermediate fluid that circulates in a closed loop through said second device.

The first device may be an oxygenator and the second device may be a cardioplegia unit.

Heat may be transferred from the supply of heat transfer fluid at the lower temperature to the supply of heat transfer fluid at the higher temperature by means of a heat pump.

The method may further comprise exchanging heat between ambient air and heat transfer fluid caused to flow through a radiator.

The hot flow circuit may comprise a first pump and a first 3-way control valve, and the cold flow circuit that comprises a second pump and a second 3-way control valve, the method further comprising: operating the first 3-way control valve to divert flow of heat transfer fluid from the hot flow circuit through the radiator so as to remove excess heat from the heat transfer fluid, and operating the second 3-way control valve to divert flow of heat transfer fluid from the cold flow circuit through the radiator so as to draw in heat to the heat transfer fluid from the ambient air.

Further alternative or optional features and advantages of the invention will become apparent from the discussion below.

DETAILED DESCRIPTION

As already discussed, currently marketed heater-cooler solutions are linked to elevated contamination risks. The present inventors have begun to address some of these issues, as set out in UK patent application Nos. GB1611409.2, GB1706563.2 and GB1707935.1, and International patent Application No. PCT/GB2017/051898, the contents of which are hereby incorporated by reference. These describe aspects of perfusion systems, including a heat exchanger arrangement for transferring heat to a fluid in an intermediate passage between a heater-cooler and a perfusion system heat exchanger. The heater-cooler systems described herein may be considered to include further refinements and/or improvements.

Described first below with reference to FIGS. 1 to 7 are embodiments that employ a heater-cooler apparatus providing separate streams of heated and cooled heat transfer fluid. Thereafter, with reference to FIGS. 8 to 15 are described embodiments of a heater-cooler apparatus employing a cold storage unit.

Figure 1A:
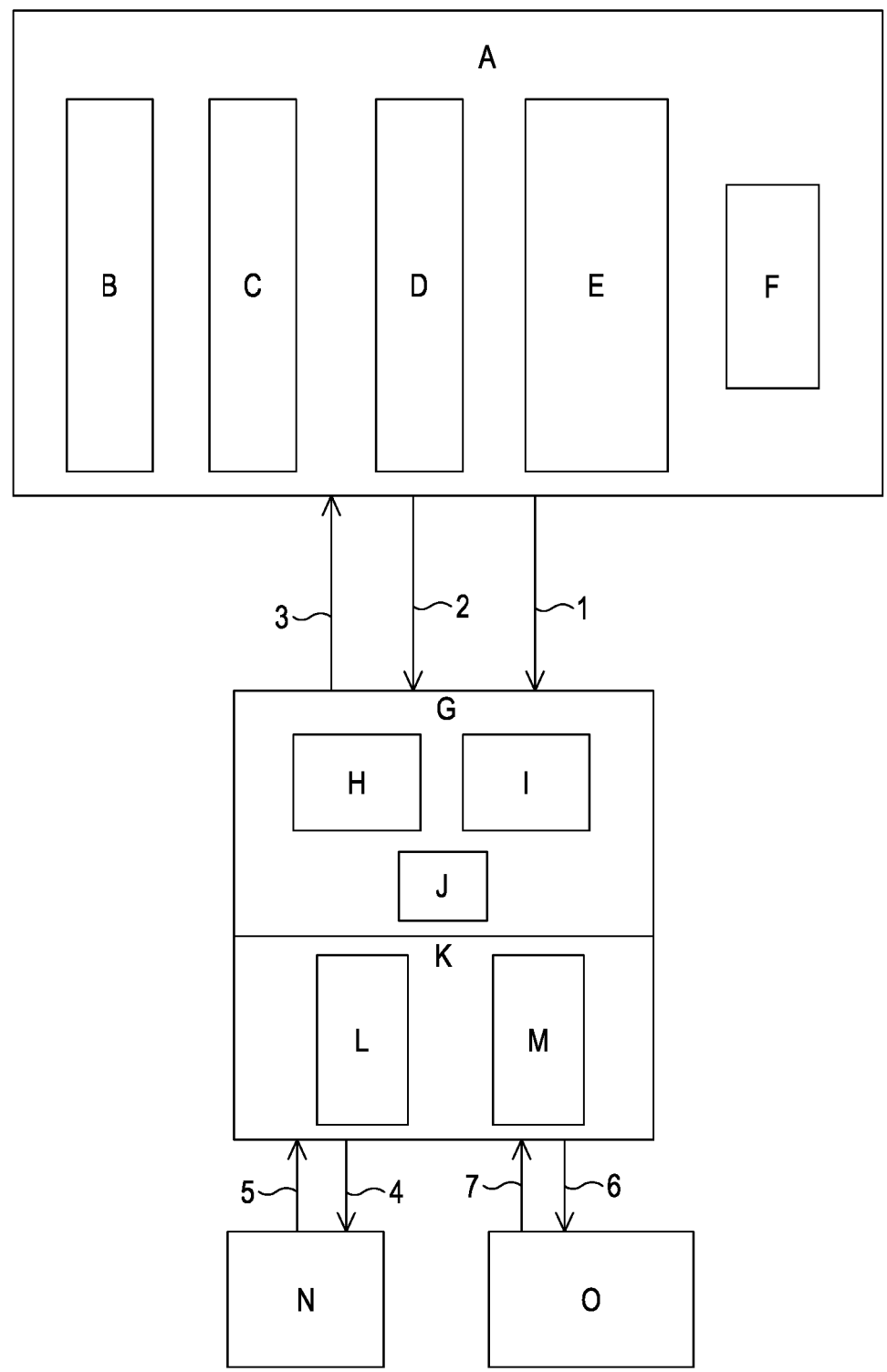
FIG. 1A is a schematic illustration of a heater-cooler system embodiment of a perfusion system.

FIG. 1A shows a schematic illustration of a heater-cooler system embodiment of a perfusion system. Note that the schematic arrangement of FIG. 1A depicts features that are described below as units or modules. This has been done to distinguish different functional aspects of the system, and should not be taken as necessarily implying that the units must be distinct or separate hardware components. The heater-cooler system includes a thermal generator unit A, a mixer unit G, an intermediate unit K, and also shows a patient cardioplegia unit N and an oxygenator unit O. The thermal generator unit A contains a radiator module B, a heat transfer fluid reservoir C, a pump module D, a refrigeration/heat (heat pump) module E and a control module F. The controller F is shown as part of the thermal generator unit A, but it will be appreciated that this could be a separate or remote controller, which exchanges data and control signals with the hardware units/modules by wired or wireless means. Three heat transfer fluid lines (e.g. hoses) 1, 2, 3 connect the thermal generator unit A with the mixer unit G. The intermediate unit K includes heat exchangers L and M which are each supplied, on one side with separate supplies of heat transfer fluid from the mixer unit G. The other side of the intermediate heat exchanger L connects with the cardioplegia unit N by means of heat transfer fluid conduits 4 and 5, and the other side of the intermediate heat exchanger M connects with oxygenator unit O by means of heat transfer fluid conduits 6 and 7. More detail of the arrangement of fluid connections within and between the units is described below with reference to FIGS. 2 to 5 and 7.

The Thermal Generator unit A generates two streams, one of hot (higher temperature) and the other of cold (lower temperature) heat transfer fluid, which are conveyed via respective fluid carrying lines or hoses 1 and 2 into the Mixer unit G where hot and cold fluids are mixed to the temperature that is demanded by the user for cooling or heating intermediate heat exchangers L and M, and in turn heat exchangers in the cardioplegia and oxygenator units N and O. Heat transfer fluid hose 3 is used for the fluid return to the thermal generator unit.

The heat transfer fluid in units A and G is preferably one that inhibits bacterial/endotoxin growth while meeting heat transfer circuit performance demands. This may be a water solution based mixture, such as a mixture of water and glycol with anti-microbial/biocidal additives. This is a first level of contamination protection in the heater-cooler system. The thermal generator and mixer unit operate closed circuits of heat transfer fluid that does not support bacteria growth and has acceptable levels of endotoxins and chemical contaminants based on application quality regulations (bacterial and endotoxin levels are those of sterile water for injection <100 Colony Forming Units (CFU)/mL; <0.25 Endotoxin Units (EU)/mL, as specified in EN ISO 13959: 2015, Water for Haemodialysis and Related Therapies). This is the first level of contamination protection provided by the heater-cooler system.

In the mixer unit G, the flow modules use hot or cold heat transfer fluid received from the thermal generator unit A and return used transfer fluid back to the unit A, achieving user demanded set point temperatures for the intermediate heat exchangers (i.e. set point temperatures correlated to the patient blood/cardioplegia heating/cooling needs).

The intermediate unit K includes the heat exchanger module L and the heat exchanger module M. These may be sealed, disposable heat exchangers carrying sterile water as a heat transfer fluid and represent a second level of contamination protection (See FIG. 7). The disposable heat exchangers L and M are preferably sterile and provided in a sterile packaged form allowing these to be connected without exposing fluid-conducting surfaces, to maintain sterility. The heat exchanger L connects with a heat exchanger in the user's patient cardioplegia unit N via sterile fluid supply hose 4 and return hose 5. The heat exchanger M connects with a heat exchanger in the user's patient oxygenator unit O via sterile fluid supply hose 6 and fluid return hose 7. Heat is exchanged from heat exchanger modules L and M to N and O based on patient heating and cooling demands, typically input by the user as a controlled temperature set point or temperature gradient until satisfactory reached and maintained.

As stated above, the units and modules shown and described above in the schematic arrangement of FIG. 1A distinguish different functional aspects of the system, and should not be taken as necessarily implying that the units must be distinct or separate hardware components. For example, the thermal generator unit A and the mixer unit G need not be physically separate, but could be incorporated into a single item of apparatus/hardware. Also, in some embodiments, the disposable heat exchangers L and M may be part of integrated disposable units that also include the fluid circuits and heat exchangers in the cardioplegia unit N and oxygenator O.

Figure 1B:
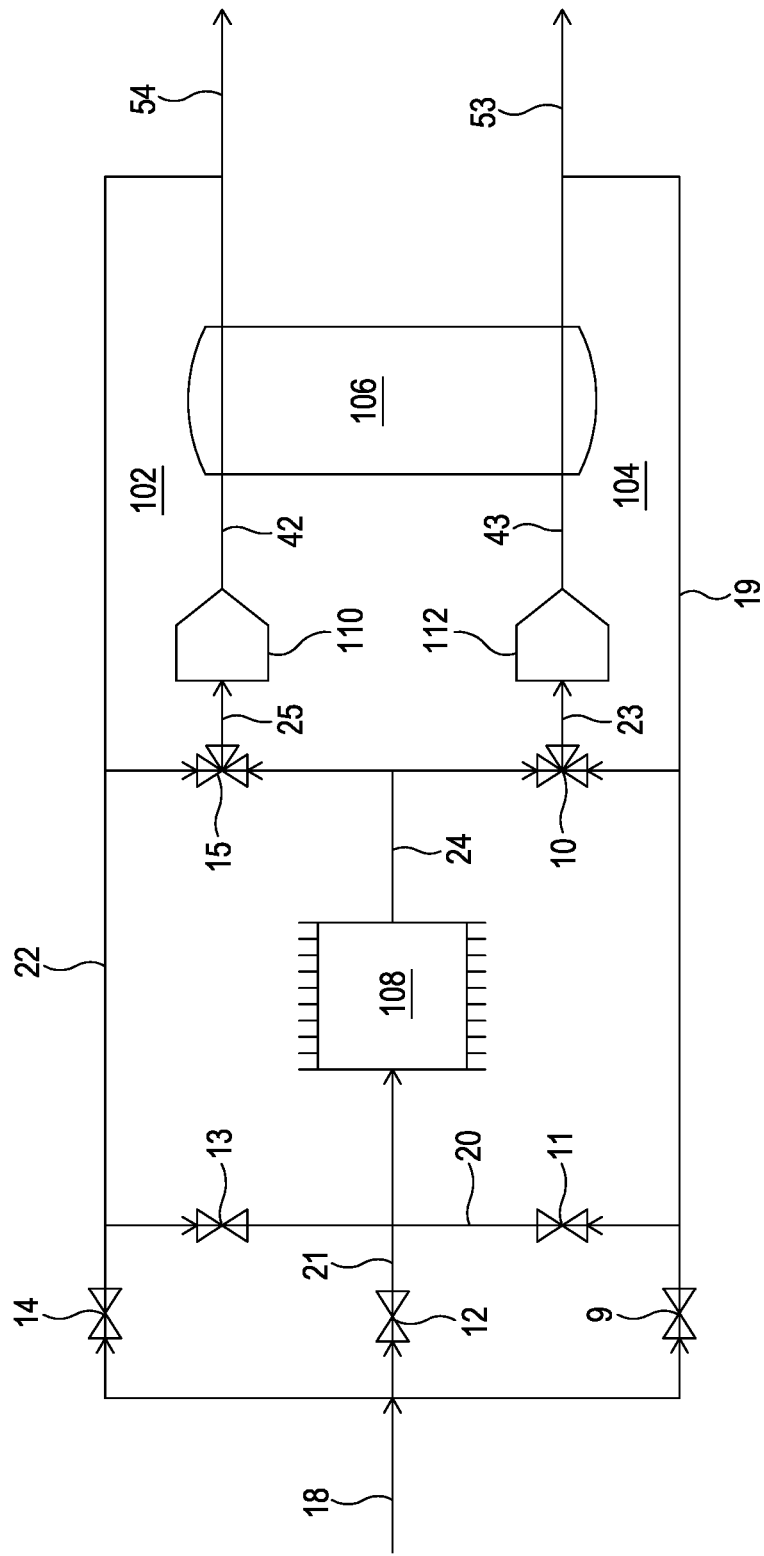
FIG. 1B shows the flow paths and principal components of an embodiment of a thermal generator of a heater-cooler system.

FIG. 1B provides an overview of the fluid and heat exchange components of a thermal generator embodiment 100, as may be employed for the thermal generator unit A of FIG. 1A. The thermal generator 100 includes a hot circuit 102 and a cold circuit 104, which provide separate flows of a hot and a cold heat transfer fluid. The terms "hot" and "cold" are not intended to represent any particular temperatures, but are relative terms—thus the hot circuit may be considered as a circuit in which the heat transfer fluid is at a higher temperature than the heat transfer fluid in the cold circuit. These flows may be provided, for example, to a mixer unit (not shown), such as mixer unit G of FIG. 1A. A hot circuit pump 110 pumps heat transfer fluid in the hot circuit and a cold circuit pump 112 pumps heat transfer fluid in the cold circuit 104.

In some embodiments, as shown in FIG. 1B, a heat pump 106 is arranged to extract heat from the heat transfer fluid in the cold circuit 104 and transfer heat into the heat transfer fluid in the hot circuit 102. Embodiments showing more details of exemplary heat pumps will be described below. The system 100 also includes a radiator 108, which exchanges heat with surrounding ambient air and is provided either for removing excess heat from, and thereby reducing the temperature of, the heat transfer fluid in the hot circuit 102, or to raise the temperature of heat transfer fluid in the cold circuit. Note that instead of a heat pump separate cooler (i.e. refrigeration) and heater units may be provided for the purpose of heating and cooling the respective hot and cold circuits 102, 104.

Also shown in FIG. 1B are valves 9-15 and fluid lines 18-25, 42, 43, 53 and 54 (for example these may be in the form of interconnecting hoses), the numbering of which is maintained in FIGS. 2-5 below. Valves 9, 11, 12, 13 and 14 are non-return valves, the direction in which flow is permitted being indicated by an arrow at the inlet side of the valve. Valves 10 and 15 are 3-way valves. Fluid line 18 is a return line from the perfusion system heat exchangers, which will be described further below.

In operation, heat transfer fluid is pumped in the hot circuit 102 by hot circuit pump 110 through heat pump 106 via line 42. At the same time heat transfer fluid is pumped in the cold circuit 104 by cold circuit pump 112 through the heat pump 106 via line 43. The heat pump 106 operates to transfer heat out of the heat transfer fluid of the cold circuit 104 and into the heat transfer fluid in the hot circuit 102. Depending on the heat/temperatures demanded by the downstream system (to be described in more detail below) some of the hot and/or cold fluid is drawn from the respective hot or cold circuits 102, 103 through lines 53, 54. Heat transfer fluid that is not drawn is circulated back through line 19 (cold circuit) or 22 (hot circuit).

The heat pump 106 will continue to operate to transfer heat from the cold circuit to the hot circuit. In order to control the temperatures of the heat transfer fluid in these circuits and prevent the system generating excessively hot or cold temperatures, some embodiments are arranged to either dump excess heat from the hot circuit or take in more heat into the cold circuit. This is done by diverting flow from one or the other of the hot and cold circuits through the radiator 108.

Control of the flow in the hot circuit 102 is achieved by the 3-way valve 15. Heat transfer fluid circulating in the hot circuit 102, and not taken off through the line 54 after flowing out of the heat pump 106 will circulate from line 22 through the 3-way valve 15 and back to the inlet of the hot circuit pump 110 when the 3-way valve 15 is at one extreme position (such that the inlet from line 24 is closed). When the 3-way valve 15 is moved so that the inlet from line 24 starts to open, some of the heat transfer fluid in line 22 starts to flow through non-return valve 13 and radiator 108. It cannot flow through non-return valves 11, 12 or 14 as this would be the wrong direction through the non-return valve. Heat from the heat transfer fluid is dissipated into the surrounding air by the radiator 108. At the other extreme position of 3-way valve 15 all the flow in line 22 will be diverted through the radiator 108 with the inlet of the 3-way valve 15 connected to line 22 being closed.

Control of flow in the cold circuit 104 operates in the same manner with 3-way valve 10 operating so that flow is diverted through non-return valve 11.

Note that the return flow in line 18 from the perfusion system heat exchangers will flow through the radiator 108 when there is flow diverted through the radiator from either of the hot or cold circuits 102, 104. When there is no flow through the radiator 108 (both the 3-way valves 10, 15 being at their extreme positions such that their inlets from line 24 are closed) then the heat transfer fluid from line 18 will flow through the non-return valves 9, 14 into the respective hot or cold circuits 102, 104. For simplicity, FIG. 1B does not show any reservoir of heat transfer fluid, such as the module C of FIG. 1A. In practice it may be preferred to include a reservoir so that a desired rate of flow of heat transfer can be maintained in each of the hot and cold circuits at all times. An exemplary reservoir system is described below with reference to FIG. 3.

Figure 2:
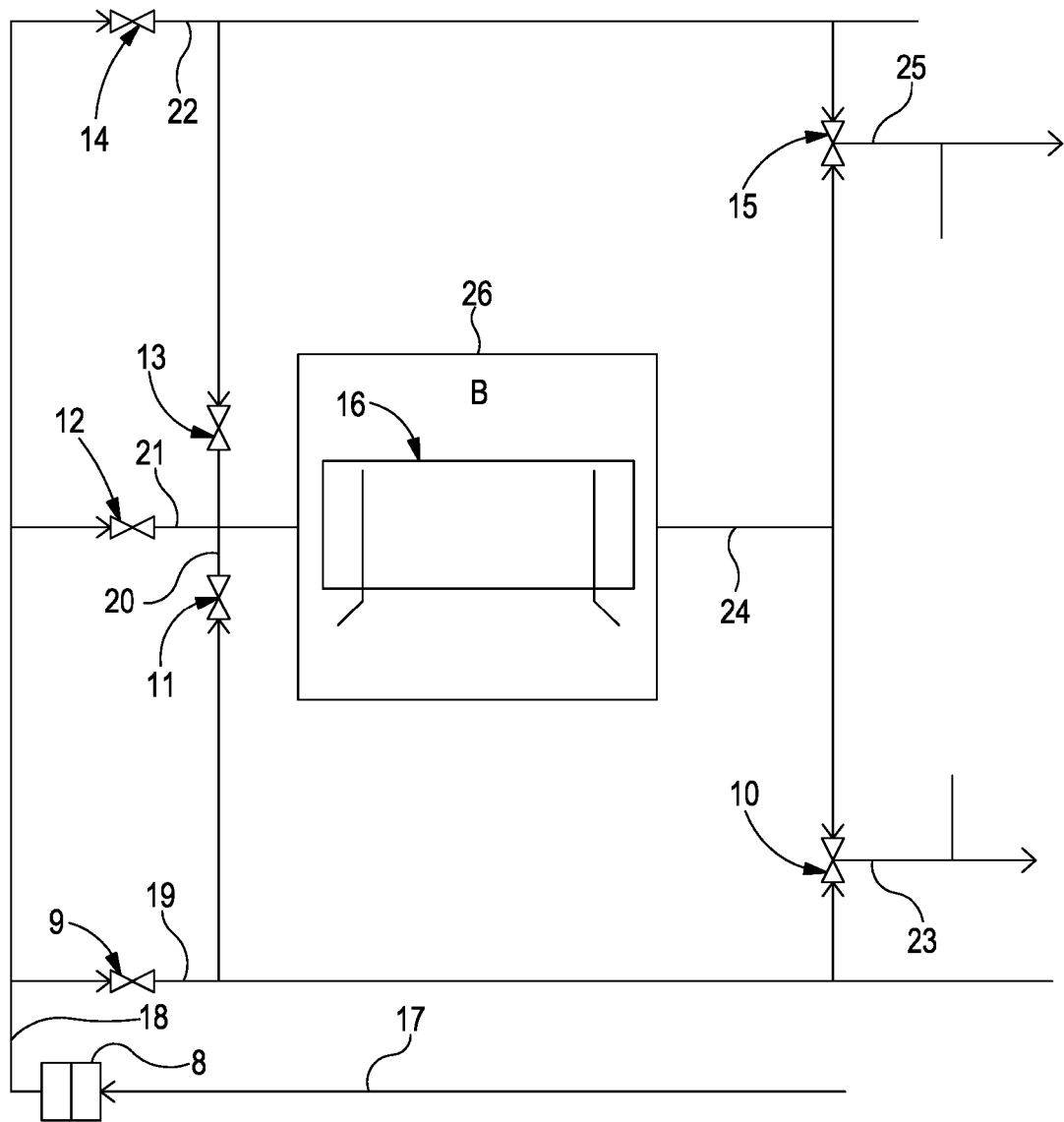
FIG. 2, shows the flow lines and components of an embodiment of a radiator module of the heater-cooler system of FIG. 1A.

Referring to FIG. 2, this shows more detail of the flow lines and components of an embodiment of the radiator module B of FIG. 1A. Items 17 to 25 are heat transfer fluid lines or hoses (the arrows indicating direction of fluid flow) and items 9 to 15 are fluid valves, as previously described with reference to FIG. 1B. Item 8 is a fluid filter. Item 16 is the radiator of module B and item 26 is an enclosure around the radiator 16. A fan (not shown) may be employed to blow air through the enclosure 16 to enhance convective heat transfer with the radiator 16. The radiator 108 of the embodiment of FIG. 1B may comprise a radiator 16 and enclosure 26 (with or without a fan) as shown in FIG. 2. Flow line 17 is the return from the perfusion heat exchangers into the filter 8, with line 18 being the low line out of the filter 8. Flow lines 19, 22, 23 and 25 connect to components of FIGS. 3, 4 and 5 as will be described below.

Figure 3:
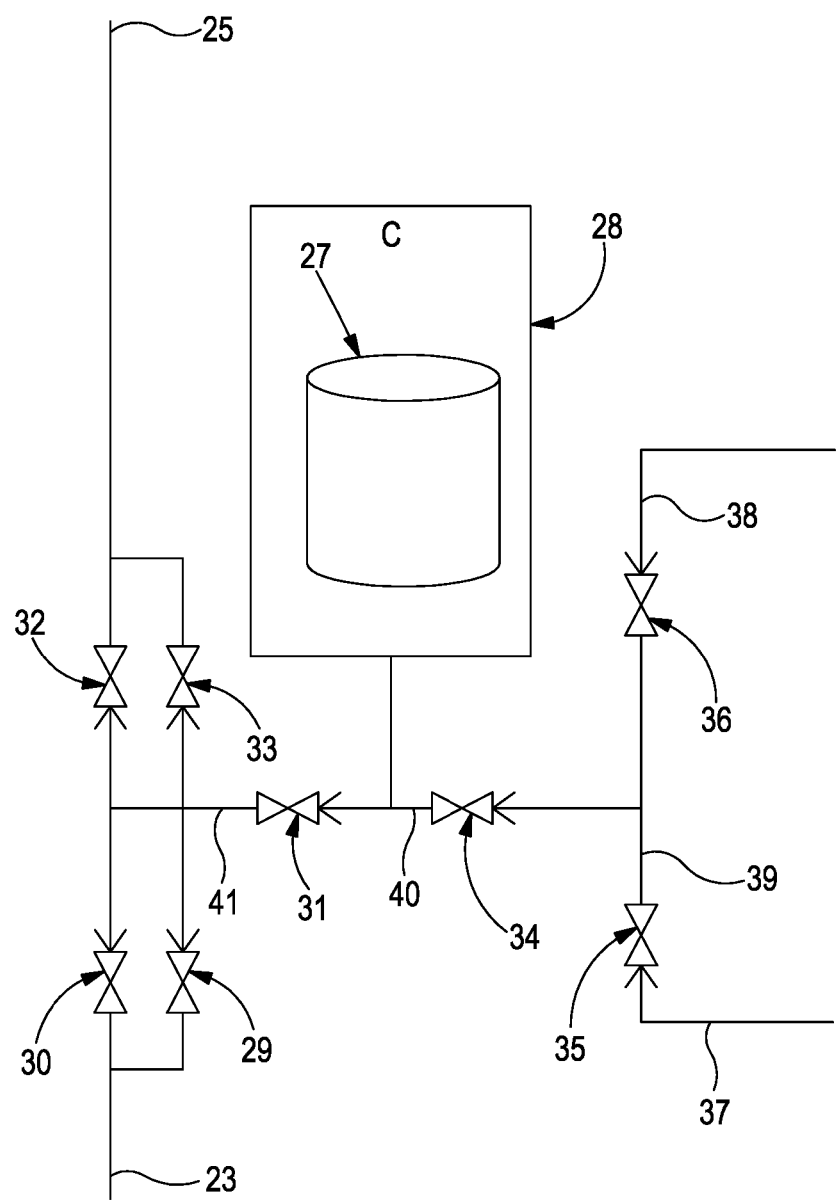
FIG. 3 shows the flow lines and components of an embodiment of a heat transfer fluid reservoir module of the heater-cooler system of FIG. 1A.

Referring to FIG. 3, this shows flow lines and components of an embodiment of the heat transfer fluid reservoir module C. Items 37, 38, 39, 40 & 41 are heat transfer fluid flow lines (hoses) with items 23 & 25 continuing from FIG. 2. Items 29 to 36 are fluid valves. Item 27 is the heat transfer fluid reservoir (module C of FIG. 1A) and item 28 is an enclosure around the reservoir 27. Each of the fluid valves shown in FIG. 3 are one-way non-return valves that permit flow only in the directions indicated by the arrows shown. Thus, when pressure of the heat transfer fluid in flow line 23 drops due to increased demand for the lower temperature fluid provided by the cold circuit 104 of FIG. 1B, fluid from the reservoir 27 will flow through fluid valves 31, 29 and 30 to replenish the fluid in the cold circuit. If there is a drop in demand for low temperature fluid provided by the cold circuit 104, excess fluid from the cold circuit will cause a rise in pressure in the circuit such that fluid will flow back into the reservoir 27 from line 37 (see FIG. 4, described further below) through fluid valves 35 and 34. In the same way, heat transfer fluid from the reservoir 27 will replenish fluid in the hot circuit 102 of FIG. 1B by flowing through fluid valves 31, 32 and 33 when pressure in the flow line 25 drops. If there is a rise in pressure in the hot circuit 102, excess fluid from the hot circuit will flow back into the reservoir 27 from line 38 (see FIG. 4, described further below) through fluid valves 36 and 34. In this way the system ensures that there is always sufficient heat transfer fluid flowing in each of the hot and cold circuits 102, 104.

In the embodiment shown in FIG. 3, one of each pair of valves 29, 30 and 32, 33 is a non-return valve, the other parallel valve in each pair is a flow restricting valve to allow for fluid to pass in either direction, but only at a very low flow rate, in case thermal expansion effects require a small reverse flow with the need for the fluid to have somewhere to go. However, other arrangements could be provided that would not require any reverse flow (for example separate devices on each of the hot and cold circuits to allow for thermal expansion).

Figure 4:
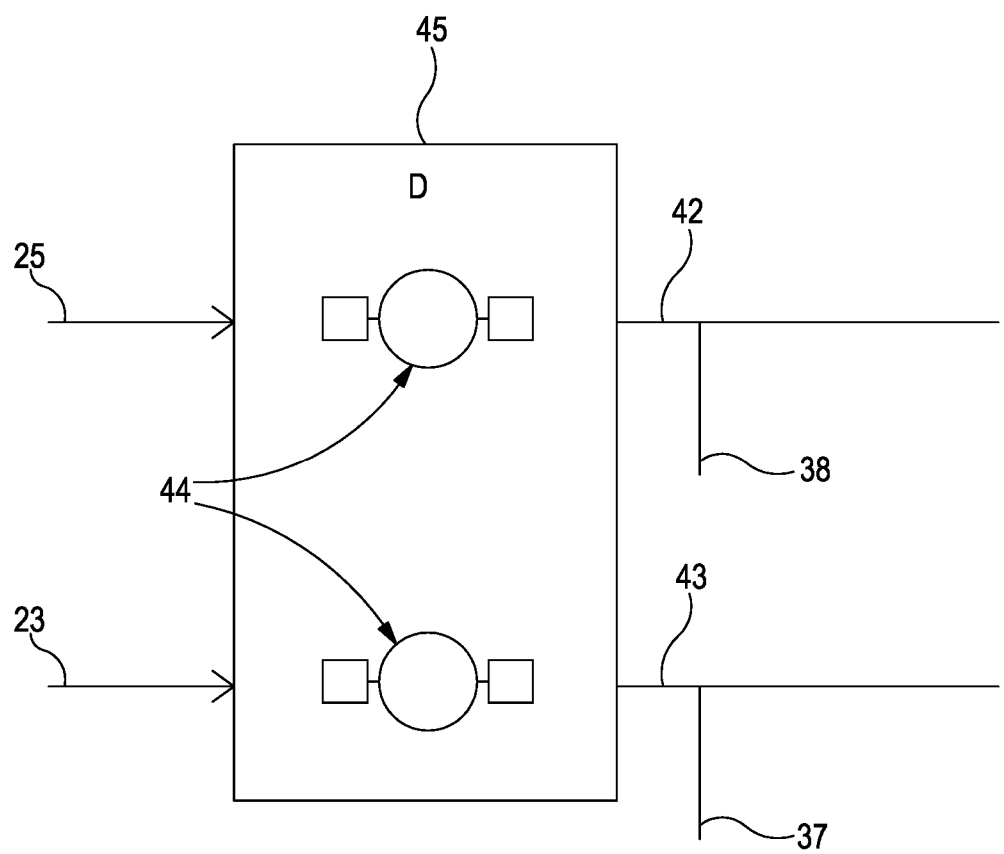
FIG. 4 shows the flow lines and components of an embodiment of a pump module of the heater-cooler system of FIG. 1A.

FIG. 4 shows the flow lines and components of an embodiment of the pump module D of FIG. 1A. Items 42 & 43 are heat transfer fluid flow lines (e.g. hoses) providing flow outlets. Items 23 and 25 are flow lines to the pump inlets for the hot and cold circuits (see FIGS. 1B, 2 and 3). Flow lines 37 & 38 are return flow branch lines back to the reservoir module C of FIG. 3. Item 44 indicates a dual pump of Module D and Item 45 is its enclosure. The dual pump 44 provides two pumped flows one for the cold circuit 104 (FIG. 1B) from line 23 to line 43 and one for the hot circuit 102 from line 25 to line 42. The dual pump 44 could be replaced by two separate pumps, such as pumps 110 and 112 shown in FIG. 1B.

As described above with reference to FIG. 3, when pressure in either of lines 42 or 43 rises due to an decrease in demand for flow in either of the hot and cold circuits, heat transfer fluid will flow back to the reservoir 27 through the respective branch lines 37, 38.

Figure 5A:
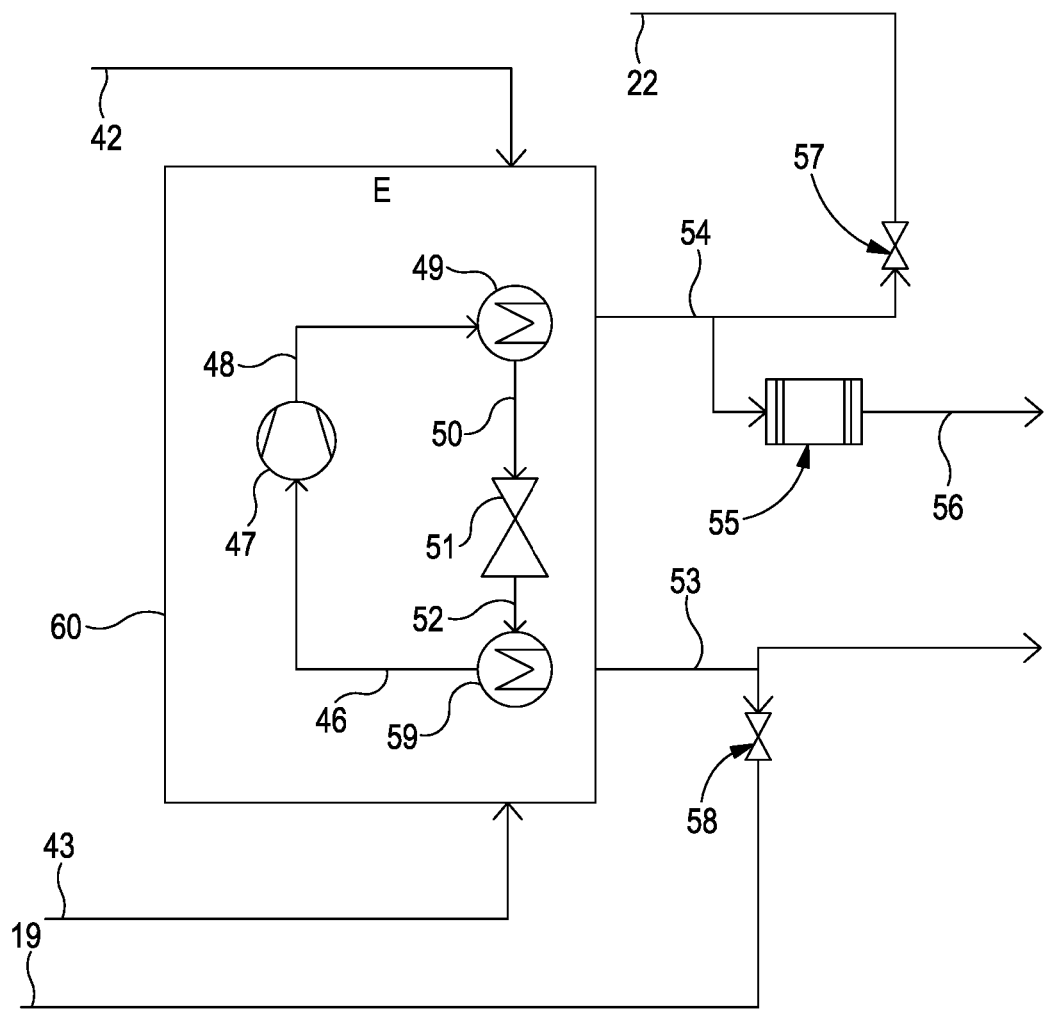
FIG. 5A shows the flow lines and components associated with an embodiment of a refrigeration/heat module of the heater-cooler system of FIG. 1A.

FIG. 5A shows the flow lines and components associated with an embodiment of the heat pump or refrigeration/heat module E of FIG. 1A. Items 19, 22, 42 and 43 are heat transfer fluid flow lines (e.g. hoses) continuing from FIGS. 2 and 4 as referred to above. Items 53, 54 and 56 are heat transfer fluid flow lines (e.g. hoses) carrying heat transfer fluid out of the heat pump module E. Items 57 & 58 are fluid valves. Item 55 is an auxiliary resistive heater for heating heat transfer fluid in line 56.

Within the heat pump module E: items 46, 48, 50 & 52 are heat exchange gas transfer lines; item 47 is a compressor; item 49 is a hot side heat exchanger and item 59 is a cold side heat exchanger; item 51 is an expansion device. Item 60 is an enclosure of the module E.

In operation heat exchange gas (i.e. refrigerant) is circulated around the heat pump driven by the compressor 47, which compresses the gas into transfer line 48 and through the hot side heat exchanger 49. The heat exchange gas from the hot side heat exchanger 49 passes through transfer line 50 and is expanded by the expansion device 51 to a low temperature, low pressure fluid, which then passes through transfer line 52 and through the cold side heat exchanger into transfer line 46 back to the inlet of the compressor 47. Heat transfer fluid in the cold circuit 104 (FIG. 1B) enters the heat pump module E through flow line 43 and passes through the cold side heat exchanger 59 where heat is extracted by the low pressure heat exchange gas that has been expanded through expansion device 51. Cooled heat transfer fluid emerges from the module through fluid flow line 53. At the same time heat transfer in the hot circuit 102 (FIG. 1B) enters the heat pump module through flow line 42 and passes through the hot side heat exchanger 49 where it is heated by compressed heat exchange gas that has been compressed by compressor 51 via transfer line 52. Heated heat transfer fluid emerges from the module through fluid flow line 54.

As referred to above, although the depicted embodiments show heat pump arrangements used for heating and cooling the heat transfer fluid in the hot and cold circuits 102,104, it will be appreciated that the same outcome may be achieved by using separate heater and cooler (refrigeration) units for the two circuits. The important requirement is for two separate controlled temperature flow circuits, one at a higher temperature and one at a lower temperature. For example, the hot circuit 102 of the heater-cooler may provide a circulating flow of heat transfer fluid at a controlled temperature in the range 30-50° C., and the cold circuit may provide a circulating flow of heat transfer fluid at a controlled temperature in the range −5-10° C.

Cold (or lower temperature) heat transfer fluid is drawn from the cold circuit via an off-take flow line 53 and hot (or higher temperature) heat transfer fluid is drawn from the hot circuit via an off-take flow line 56. These flows of heat transfer fluid may be drawn by the mixer module G to be described below with reference to FIG. 7. If there are situations where the temperature of the hot heat transfer fluid cannot be provided or maintained by the heat pump of module E, then additional heat is provided by the auxiliary heater 55. Fluid flow line 53 provides a cold (lower temperature) flow of heat transfer fluid, which may be provided to the mixer module G to be described in more detail below with reference to FIG. 7. Thus, in relation to the system of FIG. 1A, line 53 feeds into line 1. Fluid flow line 56 provides a hot (higher temperature) flow of heat transfer fluid, which may be provided to the mixer module G, and in relation to the system of FIG. 1A, line 56 feeds into line 2. Heat transfer fluid that is not drawn is circulated back through one-way non-return valves 57 and 58 into flow lines 19 and 22 respectively.

Figure 5B:
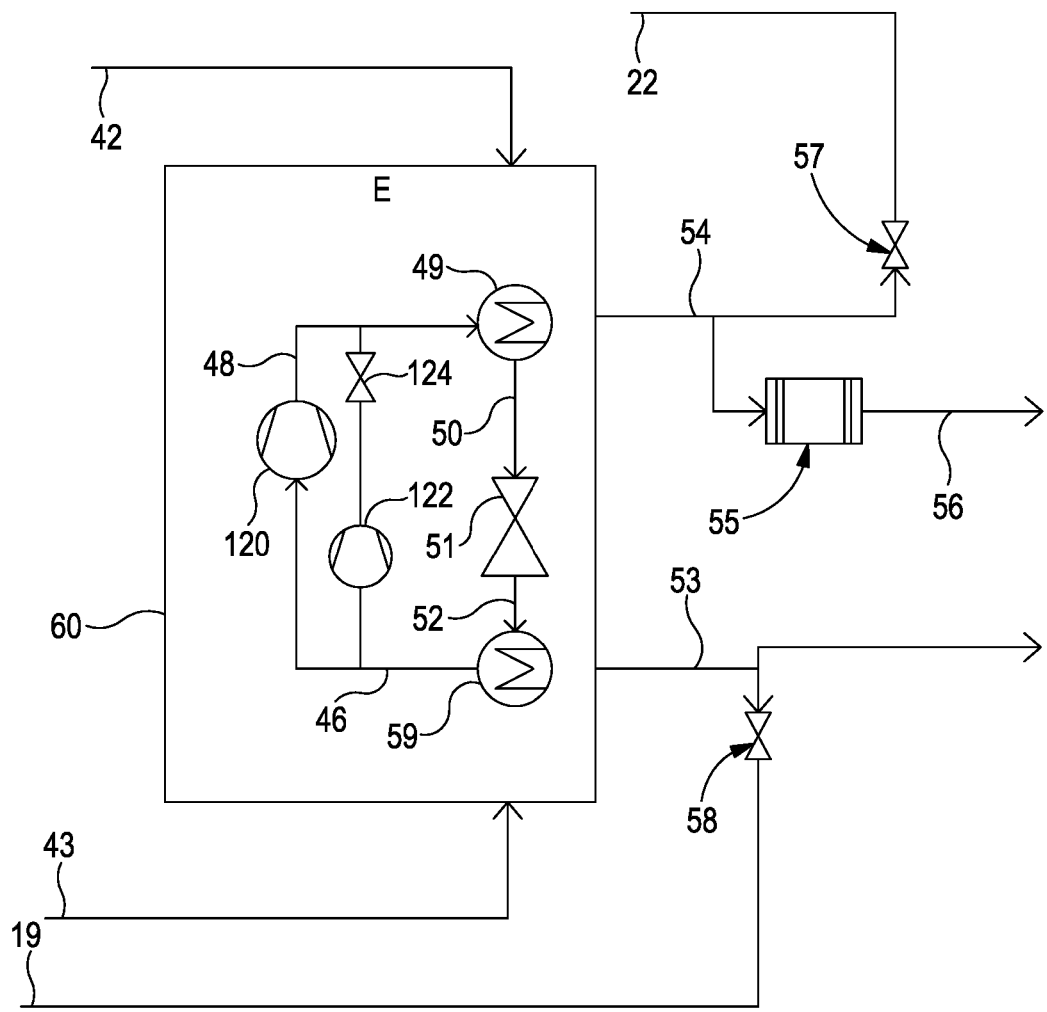
FIG. 5B shows the flow lines and components associated with an alternative embodiment of a refrigeration/heat module of the heater-cooler system of FIG. 1A.

FIG. 5B illustrates an alternative heat pump embodiment to that shown in FIG. 5A. In the embodiment of FIG. 5B, where equivalent features have the same reference numerals as used in FIG. 5A, instead of a single compressor 47, a pair of compressors 120, 122 are provided in parallel with each other and a valve 124 which can be closed to prevent flow through one of the compressors 122 when it is not operating. An advantage of using two compressors in parallel is that two smaller, and individually quieter, compressors can be used such that both compressors are run when there is a high demand for heat transfer between the hot and cold circuits, such as when the system is started, but a single compressor can be used when there is a relatively low demand. For much of the time when a perfusion system is in use in an operating theatre environment, and particularly while the surgeons are performing delicate procedures, the demand placed on the heater-cooler system is relatively low. At these times it can be important to keep the noise levels in the operating theatre environment to a minimum, which can be achieved by operating the heater-cooler system with only a single, smaller and quieter compressor.

Figure 6:
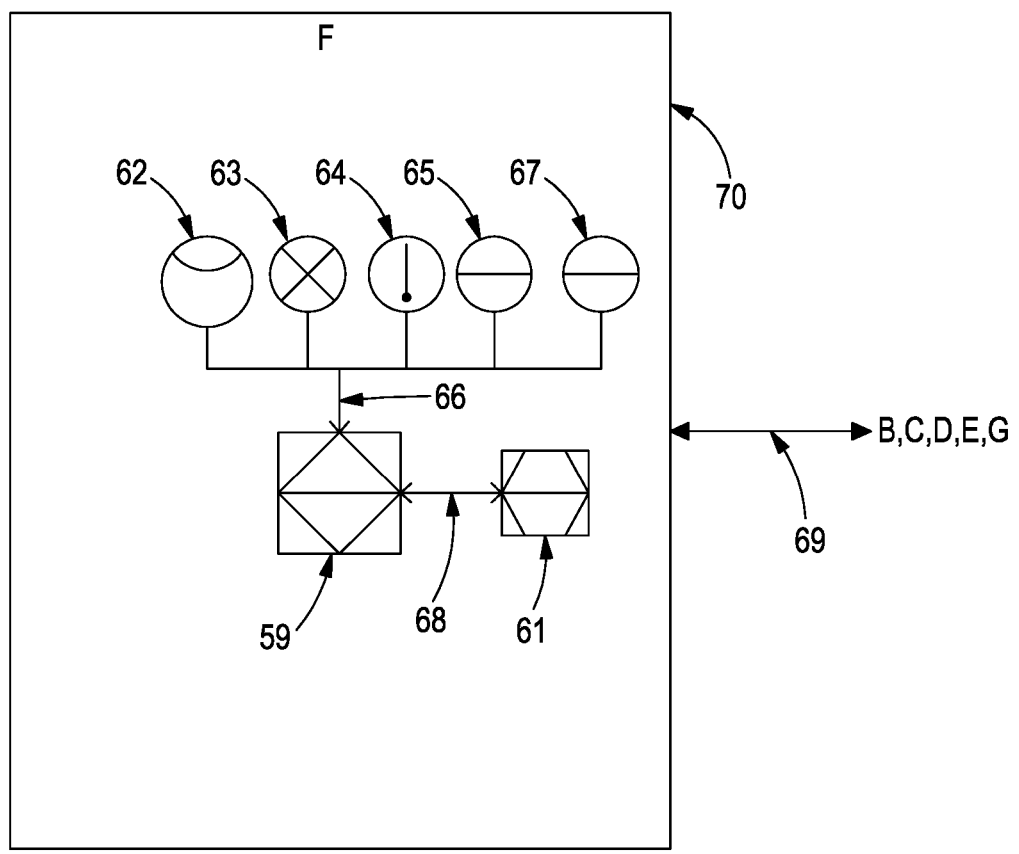
FIG. 6 is a schematic illustration of the principal components of an embodiment of a control module of the heater-cooler system of FIG. 1A.

FIG. 6, is a schematic illustration of the principal components of an embodiment of the control module F of FIG. 1A. Items 66, 67 & 68 are power and signal cabling. Item 62 is a fluid flow indicator; item 63 is a fluid pressure indicator; item 64 is a temperature indicator; item 65 is a heat transfer fluid reservoir level indicator; item 67 is an alarm indicator. Item 61 is a computer processor module and item 59 is a control unit. Item 70 is an enclosure of the control module F. Item 69 symbolises a connection means for power and communications to modules B, C, D, E and G. Suitable sensors (not shown) for sensing and monitoring fluid flow, fluid pressure, fluid temperature, and reservoir fluid level are provided at suitable locations in the heater-cooler system. Signals from these sensors are provided to the control unit 59 and the sensed values displayed by the appropriate indicators 62-66. The sensed values are also provided to the computer processor 61. Software in the computer processor 61 interprets the sensor signals and uses these to make suitable adjustments to the controlled components of the heater-cooler system, specifically the 3-way control valves 10, 15 (FIGS. 1B and 2), the pumps 110, 112 (FIGS. 1B and 4) and the auxiliary heater 55 (FIGS. 5A, 5B). If a situation arises where any of the sensed values deviates outside a normal or safe range, then the software is configured to trigger an alarm and activate the alarm indicator 67.

Note that there may be numerous medical/surgical equipment applications where the heater-cooler system described above is used to provide the higher and lower temperature heat transfer fluids through the flow lines 53 and 54. Accordingly the principles described above may find use in applications other than the perfusion system that is described herein and the apparatus described below with reference to FIG. 7. For example, the application of heat to limbs is a treatment being developed for cancer and there are many different treatments that involve taking blood out of the body and returning it to the patient that could require heating such as peripheral stem cell harvesting or dialysis.

Figure 7:
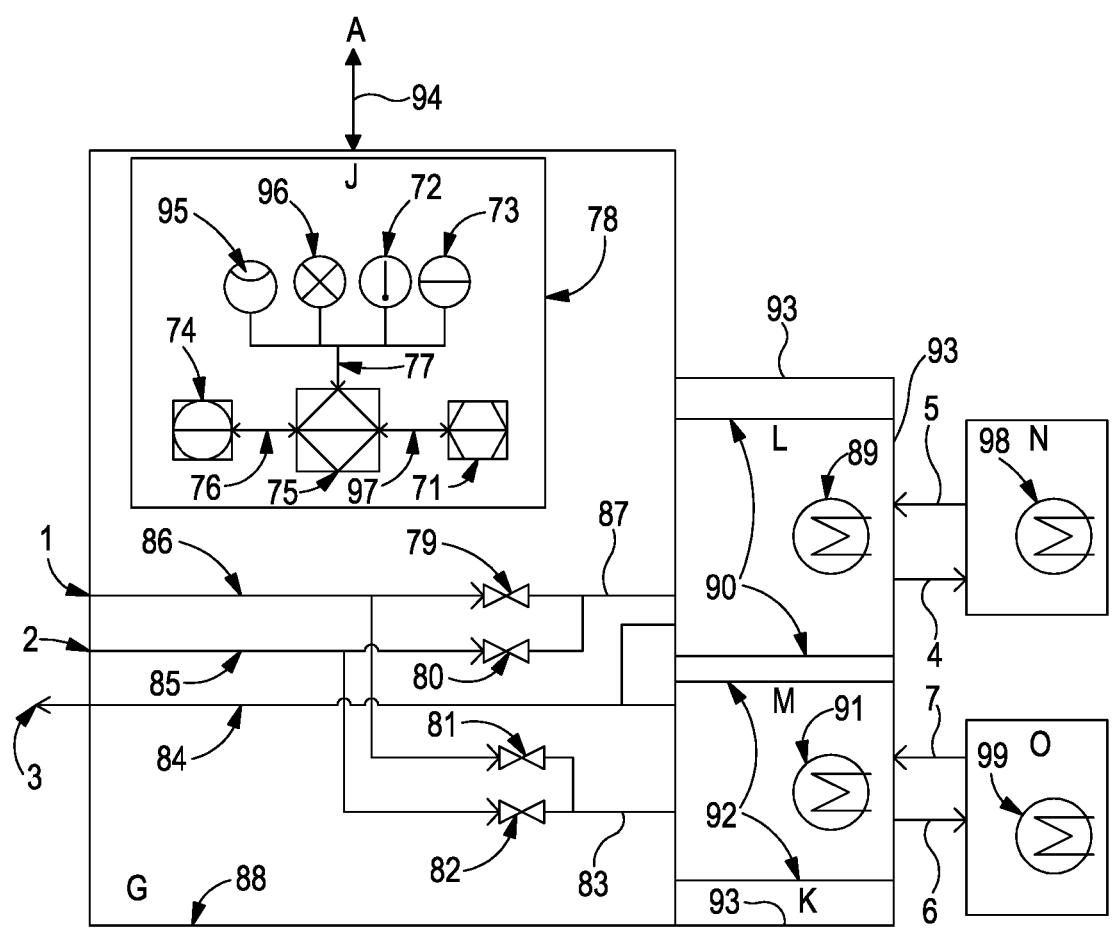
FIG. 7 shows the flow lines and components associated with an embodiment of the mixer unit G of FIG. 1A together with an associated control module J.

FIG. 7 shows the flow lines and components associated with an embodiment of the mixer unit G of FIG. 1A together with its associated control module J. Also shown, connected to the mixer unit G are heat exchanger modules L and M of unit K, which in turn connect to the heat exchangers in the cardioplegia and oxygenator units N and O.

The mixer unit G includes a cold fluid flow line 85 receiving lower temperature heat transfer fluid from line 2 (from line 53 of FIG. 5) and a hot fluid flow line 86 receiving higher temperature heat transfer fluid from line 1 (from line 56 of FIG. 5). Heat transfer fluid valves 79 and 80 are controlled to provide cold fluid from line 85 and/or hot fluid from line 86 in amounts to provide a demanded heat input to the supply side of heat exchanger module L. Similarly, heat transfer fluid valves 81 and 82 are controlled to provide cold fluid from line 85 and/or hot fluid from line 86 in amounts to provide a demanded heat input to the supply side of heat exchanger module M. Note that the demanded heat inputs to the supply sides of the heat exchanger modules may be a negative demand—i.e. the demand is for a cooling effect for heat to be removed.

The heat transfer fluid valves 79, 80, 81, 82 may be controlled in any suitable manner. For example, the valves may be controlled simply to open valve 79 while keeping valve 80 closed, to provide higher temperature fluid from line 1 when there is a demand to provide heat to raise or maintain a temperature in the cardioplegia unit N, and to open valve 80 while keeping valve 79 closed, to provide lower temperature fluid from line 2 when there is a demand to reduce heat to lower a temperature in the cardioplegia unit N. A corresponding approach may be taken for controlling the heat transfer fluid valves 81, 82 for supplying fluid to the heat exchanger module M for the oxygenator O.

In alternative control schemes the heat transfer fluid valves 79, 80, 81, 82 may be adjustably controlled to provide more or less heat transfer fluid, or to mix flows of higher temperature and lower temperature fluid to provide fluid to the heat exchanger modules L, M at a demanded temperature.

In the mixer control Module J, items 76, 97, 77 are power and signal cabling. Item 95 is a fluid flow indicator, item 96 is a fluid pressure indicator, Item 72 is a temperature indicator, item 67 is an alarm indicator, item 71 is a computer processor module and Item 75 is a control unit. Item 74 is an optional computer monitor display and item 78 is an enclosure of the control module J. Item 94 symbolises the connection means for power and communication signalling between the control unit J and other parts of the heater-cooler system.

Suitable sensors (not shown) for sensing and monitoring fluid flow, fluid pressure and fluid temperature are provided at suitable locations in the heater-cooler system. Signals from these sensors are provided to the control unit 75 and the sensed values displayed by the appropriate indicators 95, 96, 72. The sensed values are also provided to the computer processor 71. Software in the computer processor 71 interprets the sensor signals and uses these to adjust to the heat transfer fluid valves 79-82 to maintain the required flow and temperature of heat transfer fluid supplied to the heat exchanger modules L and M. If a situation arises where any of the sensed values deviates outside a normal or safe range, then the software is configured to trigger an alarm and activate the alarm indicator 73.

Heat transfer fluid leaving the heat exchanger modules L and M is returned through fluid line 3, which connects to fluid line 17 of FIG. 2.

Also shown in FIG. 7 is the intermediate unit K, which includes the heat exchanger modules L and M. Items 89 and 91 are heat exchangers, each housed within its respective enclosure 90, 92. Sterile heat exchanger fluid hoses 4 and 5 interconnect the heat exchanger 89 of unit L with a heat exchanger 98 in cardioplegia unit N and sterile heat exchanger fluid hoses 6 & 7 interconnect the heat exchanger 91 of unit M with a heat exchanger 99 in oxygenator unit O. The flow paths in which heat exchanger fluid circulates between each heat exchanger 89, 91 in units L and M and the connected heat exchangers 98, 99 in the cardioplegia and oxygenator units N and O may be in the form of sealed sterile units, such as described in the applicant's pending patent application GB1611409.2, the entire disclosure of which is hereby incorporated by reference. These sealed sterile units may be disposable units. The entire heat exchanger modules L and M may be sterile disposable units, and these may include the entire heat exchanger flow paths that connect the heat exchangers 89 and 91 with their respective heat exchangers 98 and 99 in the units N and O. The entire intermediate unit K may be a sterile disposable unit, which may include the entire heat exchanger flow paths that connect the heat exchangers 89 and 91 with their respective heat exchangers 98 and 99 in the units N and O.

As referred to above the heat transfer fluid that is provided by the thermal generator unit A of the heater-cooler system to the mixer unit G is one that inhibits bacterial growth and/or associated endotoxin release while meeting heat transfer circuit performance demands. Accordingly the fluid may be a biocidal or sterile fluid that provides a first level of contamination protection. By "biocidal", it is meant that the fluid will destroy microorganism exposed to it, e.g. because it is toxic for the microorganism. By "sterile", it is meant that the fluid is for practical purposes free of microorganisms, but if the sterile fluid becomes contaminated by microorganisms, these may quite possibly survive for some time, without however being able to thrive. The fluid may be sterile water or a water solution based mixture, for example comprising a glycol such as propylene glycol. Alternatively the heat transfer fluid may be water-less fluid such as a glycol, e.g. propylene glycol.

The intermediate unit K that includes the heat exchanger modules L and M are preferably sealed disposable heat exchanger units carrying sterile water as a heat transfer fluid and provide a second level of contamination protection. The disposable heat exchanger units may be sterile and packaged to maintain sterility. Again the heat transfer fluid in the disposable heat exchanger modules may be any biocidal or sterile fluid—sterile water, or a water solution based mixture, for example comprising a glycol such as propylene glycol, or a water-less fluid such as a glycol, e.g. propylene glycol. In embodiments the fluid circulating in the disposable heat exchanger units L and M and through the oxygenator O and cardioplegia unit N may be a biocidal fluid. For example, although glycol isn't necessarily biocidal in its nature, additives may be provided to make it so. In this way almost any suitable fluid could be made biocidal. In some embodiments the working fluid comprises a glycol (or other similar anti-freeze type compound) mixed with water (which provides the larger share of thermal mass) together with anti-corrosion and biocidal additives.

Further advantages of the heater-cooler system described above include the following.

There is no need for the thermal generator/mixer heat transfer fluid to be topped up or filled during operation or storage. This enables a substantially faster and simplified use of the equipment compared with other known equipment.

Topping up or filling also carries potential risks for contamination, which are removed.

The use of the mixer unit G enables supply of hot and cold heat exchange fluids to simultaneously demanded different cold and hot set point temperatures in the oxygenator and cardioplegia units with a rapid response to changes in the demanded set-point temperatures. For example, in some known systems ice packs are where there is a demand for low temperatures. The use ice packs is another potential source of contamination.

The use of the heat pump in the thermal generator allows for efficient use and recycling of hot and cold flows to the heat exchangers even during times of low demand.

The modular system described provides a compact design and smaller footprint than existing devices. This also allows use of multiple thermal generator units A in parallel to increase capacity and/or provide redundancy for cooling and heating demand.

Only a single air cooled radiator is required for both heating and cooling circuits.

Figure 8:
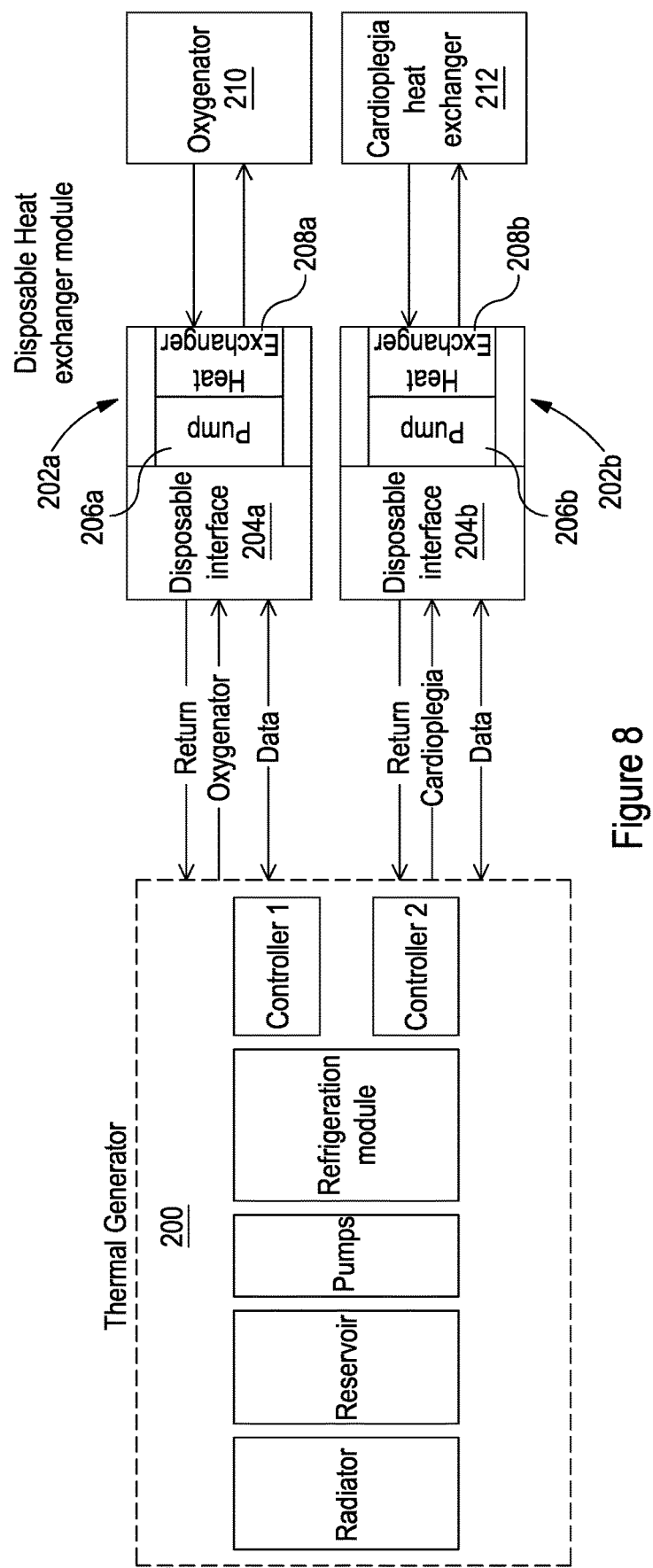
FIG. 8 is a schematic layout of another embodiment of a heater-cooler system for a perfusion system.

FIG. 8 is a schematic layout of another embodiment of a heater-cooler apparatus in an extracorporeal perfusion system. The apparatus includes a heater-cooler 200, which includes component modules similar to those described above for the embodiments of FIGS. 1 to 7, but with some differences, the details of which will be described further with reference to FIG. 11 below. Also shown in FIG. 8 are disposable heat-exchanger modules 202a, 202b.

Figure 9:
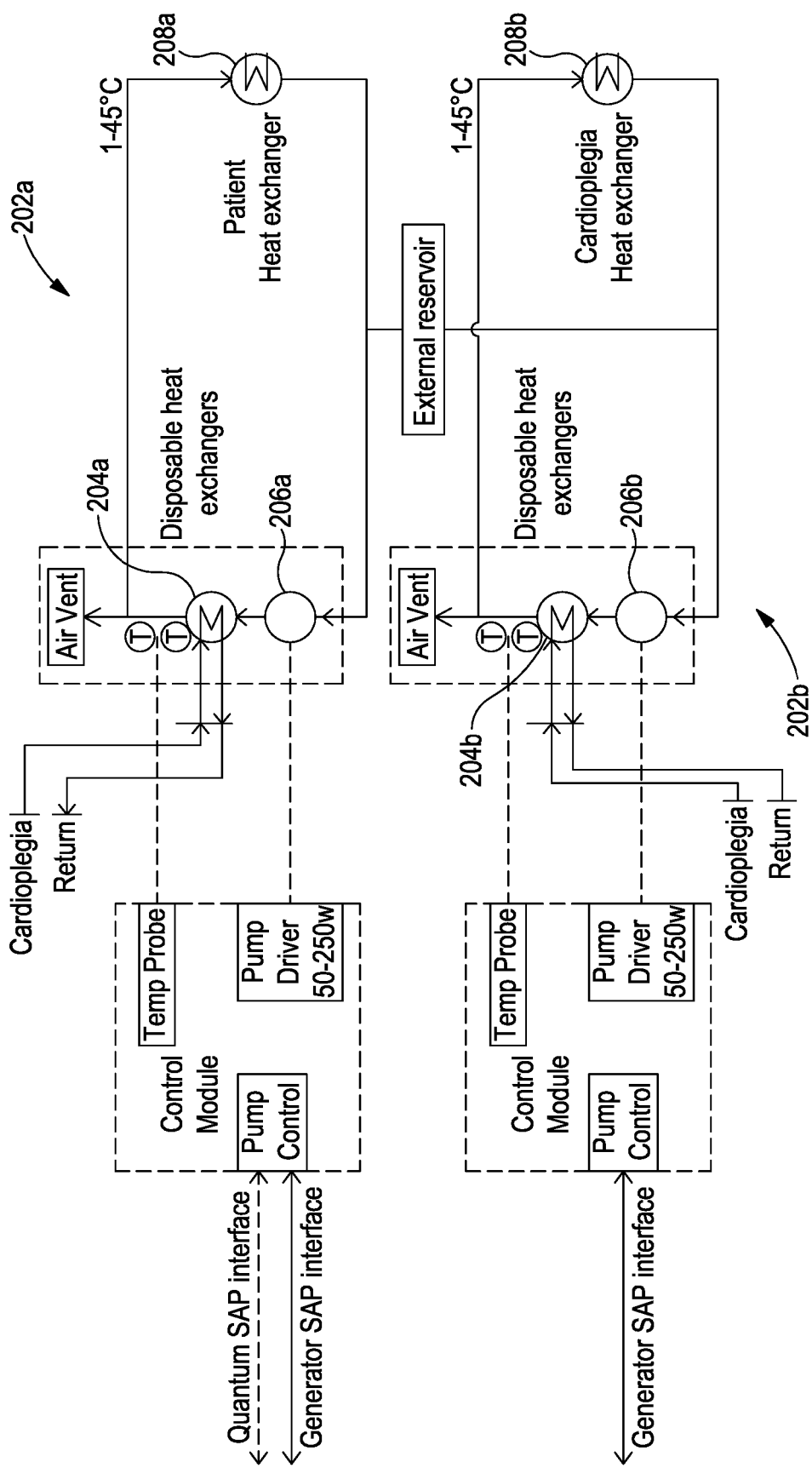
FIG. 9 is a schematic layout of still another embodiment of a heater-cooler system for a perfusion system.

FIG. 9 is a flow circuit diagram showing more detail of the fluid flow circuit and controls for the disposable heat exchanger modules 202a, 202b of the embodiment of FIG. 8. Disposable heat exchanger modules 202a, 202b each receive heat transfer fluid—for example a biocidal heat transfer fluid, such as glycol—from, and return it to, the heater-cooler 200 via disposable interfaces (heat exchangers) 204a, 204b respectively. The disposable heat exchanger modules 202a, 202b each includes a pump 206a, 206b for circulating a heat transfer fluid (e.g. sterile water) internally in a sealed loop within the heat exchanger module, which includes a heat exchanger 208a, 208b as well as the disposable interface heat exchangers 206a, 206b. Heat is exchanged in the heat exchanger 208a with a fluid (e.g. sterile water) that is supplied to an oxygenator 210 and heat is exchanged in the heat exchanger 208b with a fluid (e.g. sterile water) that is supplied to a cardioplegia heat exchanger 212. Also, as shown in FIG. 9 control modules 214a, 214b are each associated with a respective disposable heat exchanger module 202a, 202b.

Figure 10:
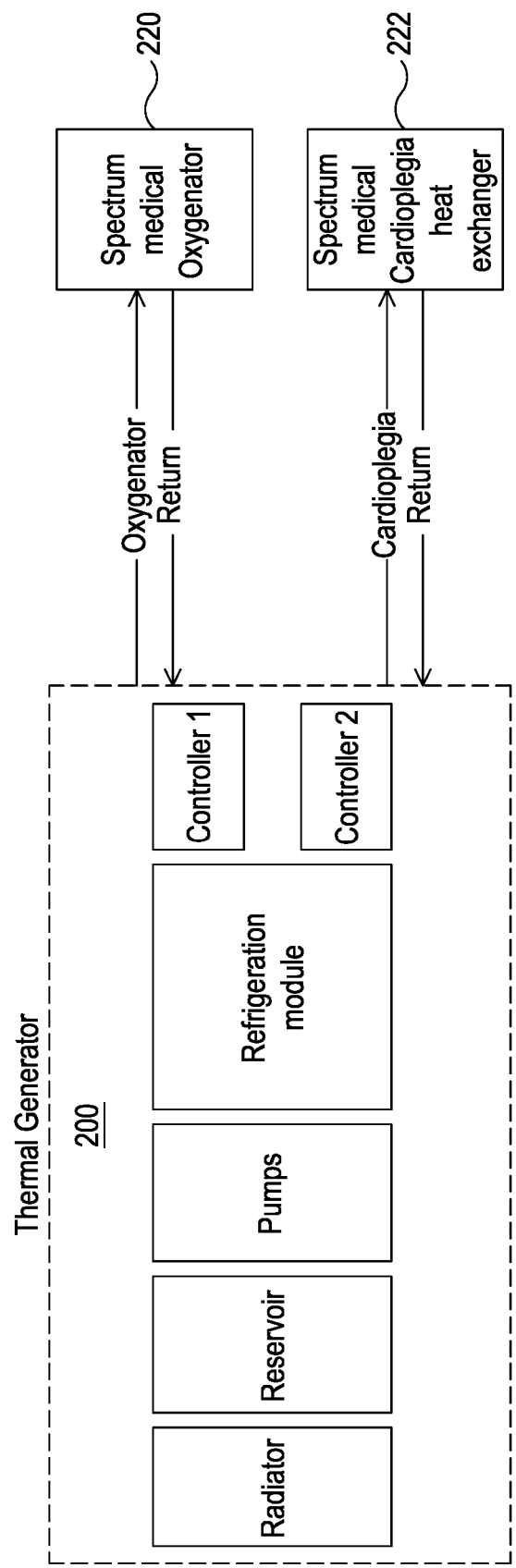
FIG. 10 is a schematic flow circuit diagram showing disposable heat exchanger modules in a perfusion system of FIG. 8.

The apparatus described in FIGS. 8 and 9 is suitable for use with many known proprietary oxygenator or cardioplegia units, which are certified for use with sterile water as the heat exchange fluid supplied to the units. FIG. 10 is a schematic layout of another embodiment, similar to that of FIG. 8, but where heat transfer fluid is supplied directly from the heater-cooler 200 to an oxygenator 220 and to a cardioplegia heat exchanger 222. Features equivalent to those of FIGS. 8 and 9 are accorded the same reference numerals. Oxygenator 220 and cardioplegia heat exchanger 222 are specially designed, and approved for use with a biocidal heat transfer fluid, such as glycol.

Figure 11:
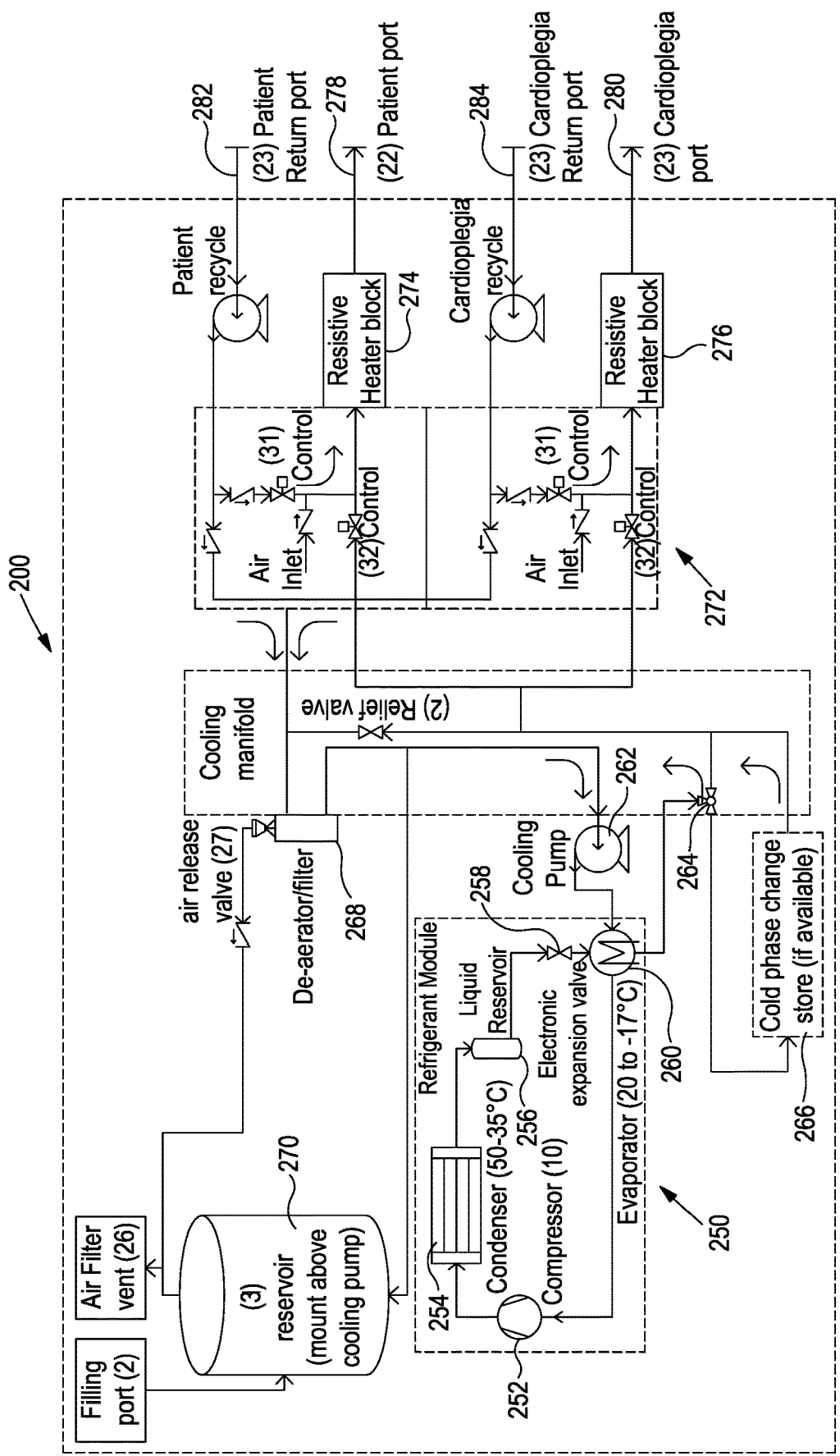
FIG. 11 is a schematic flow circuit diagram of an embodiment of a heater cooler system of FIG. 8 or 9.

FIG. 11 is a flow circuit diagram showing more detail of the fluid flow circuit and controls for the heater-cooler 200 of FIGS. 8 and 10. A refrigeration module 250, which includes a compressor 252, a condenser 254, a liquid refrigerant reservoir 256, expansion valve 258 and evaporator 260 is operable to cool a heat transfer fluid, which is preferably a biocidal heat transfer fluid, such as glycol. Also shown in FIG. 11 is a cooling pump 262, a 3/2-way valve 264 and a cold storage unit 266. In a charging mode of operation, heat transfer fluid is pumped by the cooling pump 262, through the evaporator 260 of the refrigeration module 250 where it is cooled by operation of the refrigerant in the circuit of the refrigeration unit 250. The 3/2-way valve 264 directs the cooled heat transfer fluid through the cold storage unit 266. The cold storage unit 266 is a unit that contains a material that is cooled by the heat transfer fluid but then remains at a reduced temperature ready to take in heat so as to cool a warmer heat transfer fluid when this is directed through the cold storage unit 266.

For example, the cold storage unit 266 may contain a phase change material, which when cooled changes from a liquid to a solid state and in doing so the phase change material gives up its latent heat to the heat transfer fluid. The cold storage unit 266 is then ready to receive heat from further, uncooled heat transfer fluid that is circulated through it, and in doing so to cool the heat transfer fluid. When cooling is required for a surgical operation, the heat transfer fluid is supplied through the storage unit 266 where it is cooled as it gives up heat to the frozen phase change material. An example of a phase change cold storage unit is described below with reference to FIG. 12.

As shown in FIG. 11, the refrigeration module 250, which includes a compressor 252, is within the heater-cooler 200. However, in some embodiments it is preferable for the refrigeration unit 250, and more particularly the compressor 252, to be located separately from of the other parts of the heater-cooler.

In certain surgical procedures it is desirable for there to be a laminar curtain of air surrounding the patient so as to act as a barrier to any airborne microbes contacting the patient. Compressors operate with fans that ensure the compressor does not overheat and the air flow generated by a fan can be sufficient to disrupt the laminar air curtain over the patient. Also, it can be desirable for some surgical procedures to be performed in very quiet conditions, and even a relatively quiet compressor may cause an undesirably high level of noise. Therefore, in the system shown in FIG. 11, it is possible to operate the heater-cooler apparatus 200 for long periods of time without using the compressor 252 at all. This is because a single charge of the phase change cold storage can have sufficient capacity to meet all the cooling needs. Charging of the cold storage unit 266 can take place before the surgical procedure starts.

When charging the cold storage unit 266, heat transfer fluid is circulated through the refrigeration unit 250 and cold storage unit 266, as described above. The heat transfer fluid is circulated in a closed circuit through a de-aerator and filter 268 back to the inlet of the cooling pump 262. Also shown in FIG. 11 is a reservoir 270 of heat transfer fluid. Any loss of heat transfer fluid (which may occur, for example, when the heart-cooler apparatus is disassembled and/or re-assembled between operations) can result in small amounts of air entering the fluid. The lost fluid can be replenished from the reservoir 270, and the air removed by the deaerator 268 during the charging of the cold storage unit prior to use of the system in a surgical procedure. The deaerator 268 includes an air release valve 269, the outlet of which is connected to the head space of the fluid reservoir 270. Preferably, the charging procedure is carried out prior to use of the heater-cooler 200 for a surgical procedure. This has an additional advantage over other known systems because the temperature of the fluid in the reservoir 270 does not have to be controlled during the surgical procedure.

Also shown in FIG. 11 is heat transfer fluid circuitry 272 for use during a surgical operation. Resistive heaters 274, 276 are provided for when there is a demand for heating, rather than cooling of the heat transfer fluid supplied to the perfusion system heat exchangers (not shown). FIG. 11 shows two outlets 278, 280 for providing heat transfer fluid and a corresponding two return lines 282, 284 for the heat transfer fluid, as this is circulated back to the heater-cooler 200 in closed loops. It will be appreciated that more than two, or only one, outlet and return line could be provided. Each loop of the circuitry 272 also includes an air inlet opening 286 to allow air to enter when fluid is removed. Although not show in FIG. 11, the air inlet openings 286 are preferably each connected back to the head space of the fluid reservoir 270.

Figure 12:
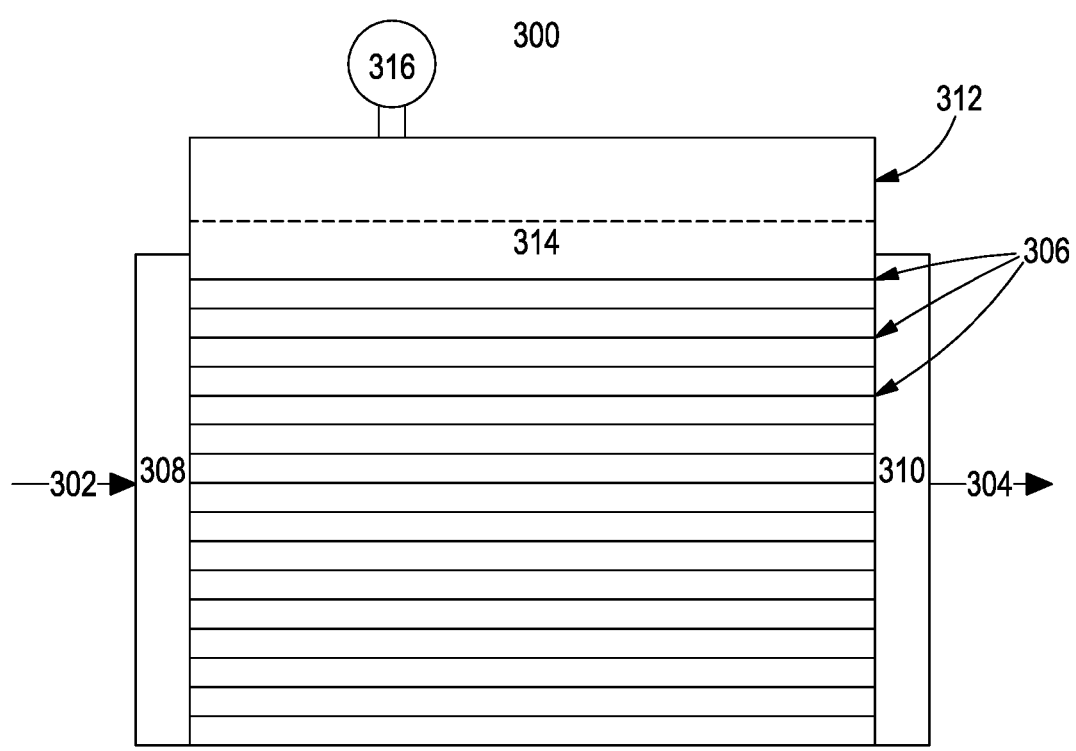
FIG. 12 shows an embodiment of a phase change cold storage unit of the heater-cooler systems of FIGS. 8 to 11.

FIG. 12 illustrates an embodiment of a cold storage unit 300, which could be used as the cold storage unit 266 of FIG. 11. An inlet 302 and an outlet 304 are provided for passage of heat transfer fluid through the cold storage unit 300. An array of tubes 306 conveys the heat transfer fluid from an inlet manifold 308 to an outlet manifold 310. The array of tubes 306 pass through a sealed chamber 312 that holds a cold storage material 314, which is preferably a liquid material having a freezing point a little below ambient temperature, a reasonably high latent heat of freezing and a low coefficient of expansion on freezing (to prevent cracking of the tubes). Water would be ideal, except for the last of these conditions. A suitable material is Rubitherm™ RT-4. Although not shown in FIG. 12, there are preferably fins extending around and between the tubes 306 to increase the heat transfer area.

When being charged, cooled heat transfer fluid is passed through the unit from the inlet 302, through the tubes 306 and to the outlet 304 of the cold storage unit 300. Heat is transferred to the heat transfer fluid from the cold storage material 314, which reduces in temperature and freezes. As it does so, the volume of the cold storage material 314 drops and so does its level. The level may be monitored by a suitable level indicator to provide an indication of the charge state of the unit 300. Alternatively, and as shown a pressure sensor 316 may be used because the pressure in the sealed chamber 312 will fall when the level falls. From the measured level or pressure, and associated state of charge it can be determined how much cooling capacity remains in the cold storage unit 300. It can also be possible, for example from known or measured flow rates and temperatures of the heat transfer fluid circulating through the system when in operation, to determine a rate of energy usage or cooling. This can then be used together with physiological data of the patient to determine a remaining available time that the cold storage unit 300 can continue to provide the required cooling. For example, the amount of cooling required will depend on the temperature to which the patient's body is to be cooled as well as the patient's size. The patient's weight, body mass index or other suitable parameter may be used to determine the amount of cooling required.

Figure 13:
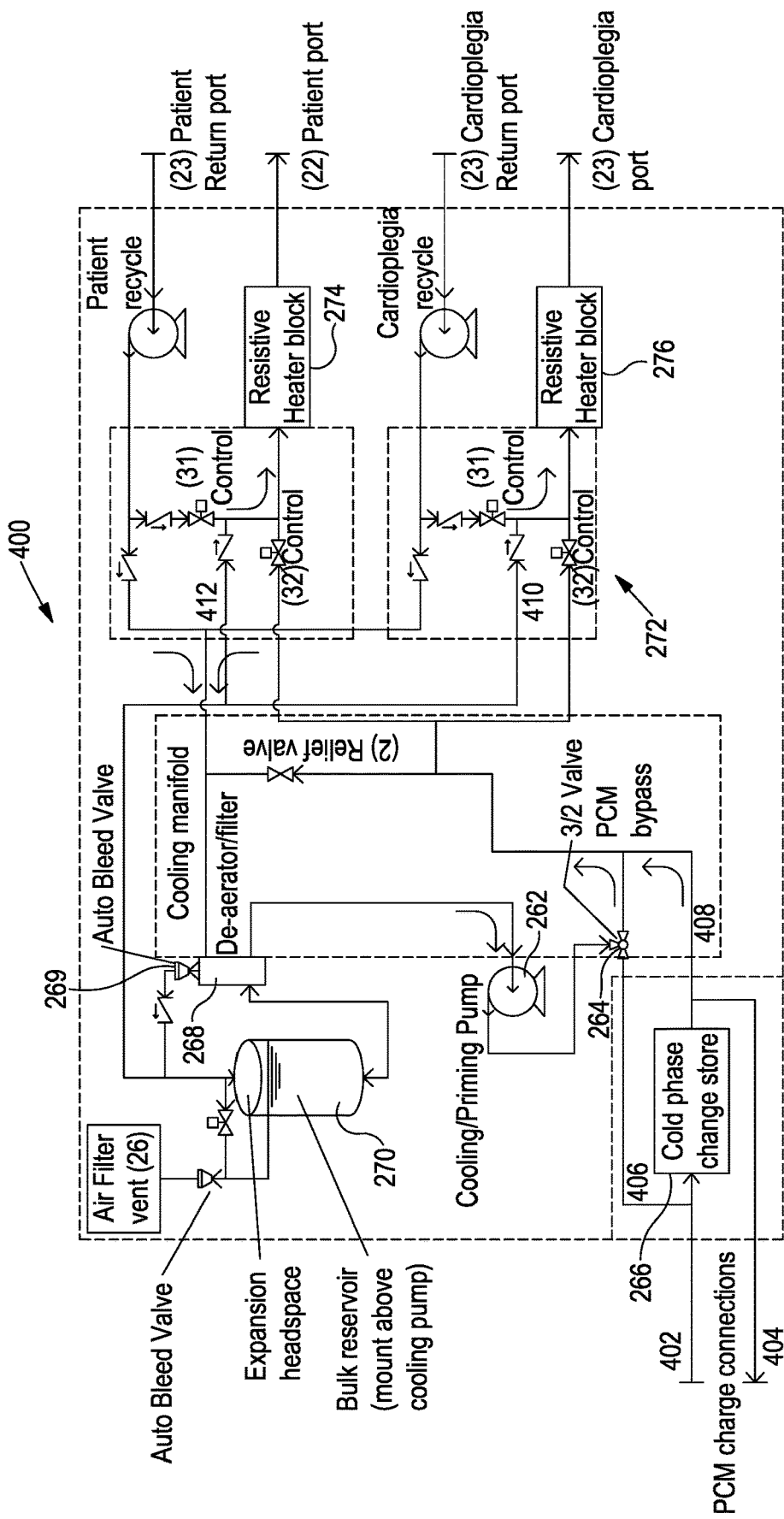
FIG. 13 is a schematic flow circuit diagram of another embodiment of a heater cooler system.

FIG. 13 shows a flow circuit diagram of another embodiment of a heater-cooler 400, similar to that of heater-cooler 200 shown in FIG. 11. Equivalent features have the same reference numerals. In the embodiment of FIG. 13, the heat transfer fluid is supplied to the cold storage unit 266 from two separate sets of inlet and outlet connections. One set of connections 402, 404 is used to connect the cold storage unit 266 to an external circuit for charging, while the other set of connections 406, 408 is used for passing heat transfer fluid through the cold storage unit to provide cooling of the fluid during use in a surgical procedure. FIG. 13 also shows air inlets 410, 412 in the circuitry 272 connected to the air venting arrangement associated with the reservoir 270.

Figure 14:
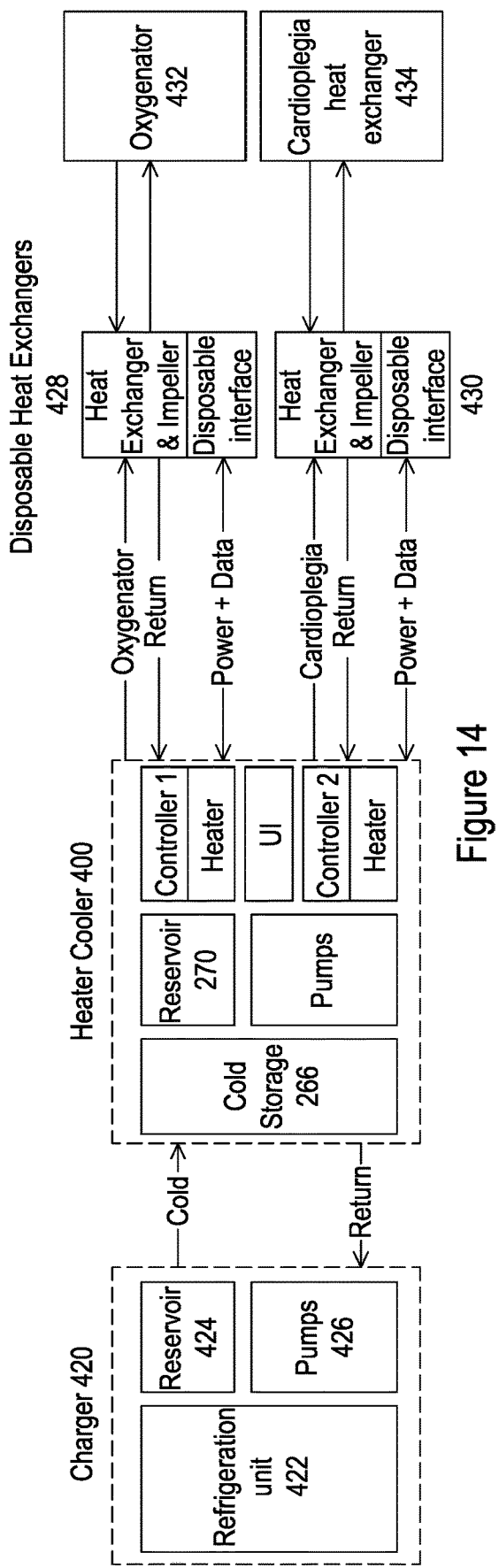
FIG. 14 is a schematic layout of an embodiment of a perfusion system including the heater-cooler system of FIG. 13.
Figure 15:
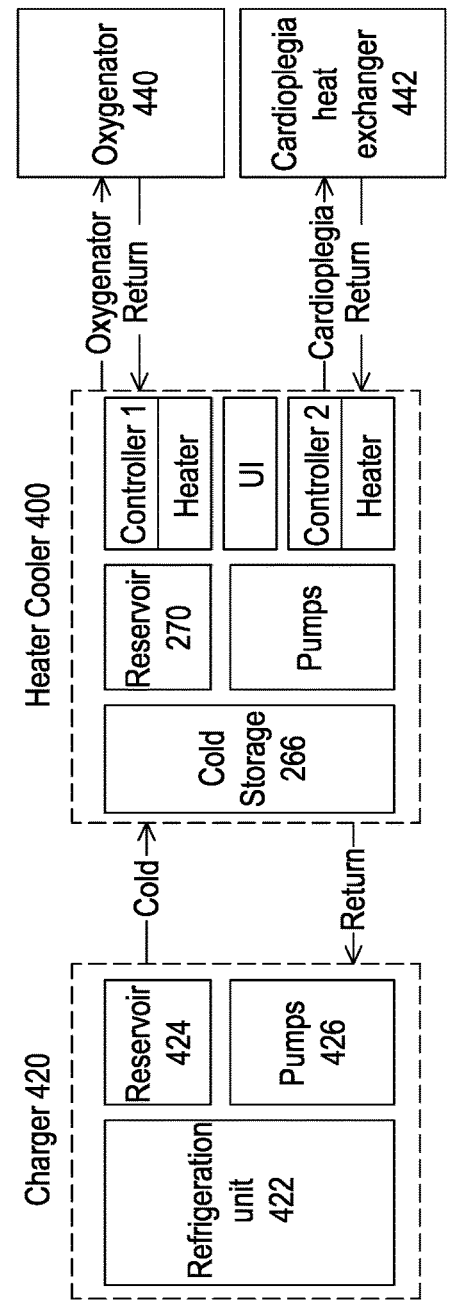
FIG. 15 is a schematic layout of another embodiment of a perfusion system including the heater-cooler system of FIG. 13.

FIGS. 14 and 15 illustrate two alternative arrangements for use of the heater-cooler 400 of FIG. 13. In both the embodiments of FIGS. 13 and 14 a separate charger unit 420, which includes a refrigeration unit 422, a heat transfer fluid reservoir 424 and associated pumps 426, supplies cooled fluid for charging the cold storage unit 266 of the heater-cooler 400.

In the embodiment of FIG. 14 the heater-cooler 400 supplies heated or cooled heat transfer fluid to intermediate disposable heat exchanger modules 428, 430. One module 428 is connected to an oxygenator 432 and the other module 430 is connected to a cardioplegia unit 434. In this embodiment the intermediate heat exchangers 428, 430 exchange heat of the heat transfer fluid with a fluid such as sterilised water, which is supplied to the oxygenator 432 and/or cardioplegia unit 434. This allows the heater-cooler 400 to be used with existing/proprietary oxygenators and cardioplegia units which may only be certified for use with sterilised water.

In the embodiment of FIG. 15, the heat transfer fluid is provided directly to an oxygenator 440 and cardioplegia unit 442. In this case it is advantageous that the heat transfer fluid is a biocidal fluid such as glycol, therefore eliminating another potential source of microbial ingress. The oxygenator 440 and cardioplegia unit 442 are units that are approved for use with the biocidal fluid.

In the embodiments of both FIG. 14 and FIG. 15, where a separate charger unit 420 is used, the heat transfer fluid reservoir 270 in the heater-cooler 400 can be topped up from the flow of heat transfer fluid during the charging stage.

The invention claimed is:

1. A heater-cooler apparatus for an extracorporeal perfusion system, the heater-cooler apparatus comprising:
   a cold storage unit;
   a refrigeration unit configured to charge the cold storage unit; and
   at least one fluid circuit configured to (i) direct a heat transfer fluid through the refrigeration unit to cool the heat transfer fluid, (ii) direct the heat transfer fluid cooled by the refrigeration unit through the cold storage unit from the refrigeration unit to the cold storage unit to charge the cold storage unit, and (iii) provide the heat transfer fluid to the extracorporeal perfusion system,
   wherein the cold storage unit comprises a chamber containing a liquid that freezes at a temperature above that to which the heat transfer fluid is cooled by the refrigeration unit, and a passage through which the heat transfer fluid is conveyed, the passage extending through the chamber.

2. The heater-cooler apparatus of claim 1, wherein the cold storage unit comprises a non-water-based phase change material that freezes when cooled.

3. The heater-cooler apparatus of claim 1, wherein the at least one fluid circuit is further configured to direct the heat transfer fluid through the cold storage unit to cool the heat transfer fluid for use in the extracorporeal perfusion system without the heat transfer fluid being cooled by the refrigeration unit.

4. The heater-cooler apparatus of claim 1, wherein the heater-cooler apparatus comprises an integral unit that includes the refrigeration unit.

5. The heater-cooler apparatus of claim 1, wherein the refrigeration unit is provided as a separate unit for supplying a flow of cooled heat transfer fluid to charge the cold storage unit.

6. The heater-cooler apparatus of claim 1, further comprising one or more heaters for heating the heat transfer fluid.

7. The heater-cooler apparatus of claim 1, comprising a plurality of fluid circuits for supplying heat transfer fluid to a plurality of heat exchangers of the perfusion system.

8. The heater-cooler apparatus of claim 1, wherein the heat transfer fluid is a biocidal fluid.

9. The heater-cooler apparatus of claim 8, wherein the biocidal fluid comprises glycol.

10. The heater-cooler apparatus of claim 8, wherein the at least one fluid circuit is configured to provide heat transfer fluid directly from the heater-cooler apparatus to heat exchangers of the extracorporeal perfusion system.

11. The heater-cooler apparatus of claim 1, wherein the at least one fluid circuit is configured to provide heat transfer fluid to a disposable heat-exchanger module supplied with the heat transfer fluid from the heater-cooler apparatus.

12. The heater-cooler apparatus of claim 1, wherein the passage comprises an array of tubes through which the heat transfer fluid is conveyed, the array of tubes extending through the chamber.

13. The heater-cooler apparatus of claim 12, wherein the cold storage unit further comprises fins extending around and between tubes of the array of tubes.

14. The heater-cooler apparatus of claim 12, further comprising a sensor configured to provide an indication of a state of charging of the cold storage unit.

15. The heater-cooler apparatus of claim 14, wherein the sensor is a level sensor configured to measure a level of the cold storage material in the cold storage unit, or a pressure sensor configured to measure a pressure in the chamber of the cold storage unit.

16. The heater cooler apparatus of claim 14, further comprising a controller configured to determine a duration of operation of the apparatus based on the determined state of charge and on one or more physiological parameters of a patient.

17. The heater-cooler apparatus of claim 15, wherein the physiological parameters comprise a weight of the patient or a body mass index of the patient.

18. The heater-cooler apparatus of claim 1, further comprising:
a circuit configured to circulate the heat transfer fluid through a de-aerator and filter; and
a reservoir of heat transfer fluid to replenish heat transfer fluid in the heater-cooler apparatus.

19. A method of operating a heater-cooler apparatus including a cold storage unit, a refrigeration unit configured to charge the cold storage unit, and at least one fluid circuit configured to (i) direct a heat transfer fluid through the refrigeration unit to cool the heat transfer fluid, (ii) direct the heat transfer fluid cooled by the refrigeration unit through the cold storage unit from the refrigeration unit to the cold storage unit to charge the cold storage unit, and (iii) provide the heat transfer fluid to the extracorporeal perfusion system, and a passage through which the heat transfer fluid is conveyed, the passage extending through a chamber in the cold storage unit, the method comprising:
a charging stage, including:
operating the refrigeration unit to charge the cold storage unit to change a liquid in the chamber of the cold storage unit to a solid state; and
ceasing operation of the refrigeration unit; and
an operating stage including:
directing the heat transfer fluid through the cold storage unit to cool the heat transfer fluid for supplying the extracorporeal perfusion system via the at least one fluid circuit, wherein the chamber contains the liquid that freezes at a temperature above that to which the heat transfer fluid is cooled by the refrigeration unit.

20. The method of claim 19 further comprising monitoring a state of charge of the cold storage unit.

21. The method of claim 20, wherein the state of charge of the cold storage unit is monitored by measuring a level of the cold storage material in the cold storage unit, or by measuring a pressure in the chamber of the cold storage unit.

22. The method of claim 21, further comprising determining a duration of operation of the heater-cooler apparatus based on the state of charge and on one or more physiological parameters of a patient.

23. The method of claim 22, wherein the physiological parameters comprise a weight of the patient or a body mass index of the patient.

24. The method of claim 19, further comprising filling a heat transfer fluid reservoir of the heater-cooler system during the charging stage.

* * * * *